United States Patent
Vaccaro et al.

(10) Patent No.: US 10,363,401 B2
(45) Date of Patent: *Jul. 30, 2019

(54) SINUS DILATION SYSTEM AND METHOD

(71) Applicant: Medtronic Xomed, Inc., Jacksonville, FL (US)

(72) Inventors: Robert K. Vaccaro, Ponte Vedra Beach, FL (US); Charles Franklin Scott Carpenter, Neptune Beach, FL (US); David J. Little, II, Ponte Vedra, FL (US); Ali Mowlai-Ashtiani, Jacksonville, FL (US); Matthew J. Nadeau, Lafayette, CO (US); Dana A. Oliver, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 279 days.

This patent is subject to a terminal disclaimer.

(21) Appl. No.: 15/271,427

(22) Filed: Sep. 21, 2016

(65) Prior Publication Data

US 2017/0007811 A1 Jan. 12, 2017

Related U.S. Application Data

(63) Continuation of application No. 13/725,716, filed on Dec. 21, 2012, now Pat. No. 9,463,307.

(51) Int. Cl.
*A61B 17/24* (2006.01)
*A61M 29/02* (2006.01)
(Continued)

(52) U.S. Cl.
CPC ............. *A61M 29/02* (2013.01); *A61B 17/24* (2013.01); *A61B 34/20* (2016.02); *A61B 90/90* (2016.02);
(Continued)

(58) Field of Classification Search
CPC .......... A61M 2210/0681; A61M 29/02; A61B 17/24; A61B 17/12104; A61B 19/5244;
(Continued)

(56) References Cited

U.S. PATENT DOCUMENTS 5,108,404 A 4/1992 Scholten et al.
5,766,151 A 6/1998 Valley et al.
(Continued)

FOREIGN PATENT DOCUMENTS

CN 102458553 A 5/2012
EP 1504713 2/2005
(Continued)

OTHER PUBLICATIONS

International Search Report and Written Opinion for PCT/US2013/076120 dated Mar. 20, 2014.

*Primary Examiner* — Ryan J. Severson
*Assistant Examiner* — Christian D Knauss
(74) *Attorney, Agent, or Firm* — Dicke, Billig & Czaja, PLLC

(57) ABSTRACT

A sinus dilation instrument useful with a navigation system and including a handle, a rigid probe, a balloon, and an identifier device. The probe extends from the handle, forms a curved segment, and carries the balloon. The identifier device is programmed to generate a signal indicative of an instrument identification assigned to the instrument, and is a frontal, maxillary or sphenoid sinus instrument. The signal is formatted to be recognized by an IGS. Once connected, the IGS recognizes the instrument and can retrieve information indicative of a spatial location of the balloon, for example via an instrument tracking device. A surgeon can "plug and play" the sinus dilation instrument with the IGS to perform a procedure.

14 Claims, 15 Drawing Sheets

(51) Int. Cl.
*A61B 34/20* (2016.01)
*A61B 90/90* (2016.01)
*A61B 90/98* (2016.01)
*A61B 17/00* (2006.01)

(52) U.S. Cl.
CPC .... *A61B 90/98* (2016.02); *A61B 2017/00482* (2013.01); *A61B 2034/2051* (2016.02); *A61B 2034/2065* (2016.02)

(58) Field of Classification Search
CPC .. A61B 2019/5251; A61B 2017/00225; A61B 2017/0046; A61B 2017/00464; A61B 2017/00473; A61B 2017/22072; A61B 34/20; A61B 2034/2051; A61B 90/90; A61B 90/98
See application file for complete search history.

(56) References Cited

U.S. PATENT DOCUMENTS

| | | |
|---|---|---|
| 5,972,015 A | 10/1999 | Scribner et al. |
| 6,248,110 B1 | 6/2001 | Reiley et al. |
| 6,280,456 B1 | 8/2001 | Scribner et al. |
| 6,623,505 B2 | 9/2003 | Scribner et al. |
| 6,979,341 B2 | 12/2005 | Scribner et al. |
| 7,156,861 B2 | 1/2007 | Scribner et al. |
| 7,462,175 B2 | 12/2008 | Chang et al. |
| 7,500,971 B2 | 3/2009 | Chang et al. |
| 7,520,876 B2 | 4/2009 | Ressemann et al. |
| 7,641,644 B2 | 1/2010 | Chang et al. |
| 7,645,272 B2 | 1/2010 | Chang et al. |
| 7,654,997 B2 | 2/2010 | Makower et al. |
| 7,678,099 B2 | 3/2010 | Ressemann et al. |
| 7,717,933 B2 | 5/2010 | Becker |
| 7,720,521 B2 | 5/2010 | Chang et al. |
| 7,727,186 B2 | 6/2010 | Makower et al. |
| 7,727,226 B2 | 6/2010 | Chang |
| 7,740,642 B2 | 6/2010 | Becker |
| 7,753,929 B2 | 7/2010 | Becker |
| 7,753,930 B2 | 7/2010 | Becker |
| 7,771,409 B2 | 8/2010 | Chang et al. |
| 7,803,150 B2 | 9/2010 | Chang et al. |
| 7,836,888 B2 | 11/2010 | Hegde et al. |
| 7,854,747 B2 | 12/2010 | Becker |
| 7,879,061 B2 | 2/2011 | Keith et al. |
| 7,918,871 B2 | 4/2011 | Truitt et al. |
| 7,971,341 B2 | 7/2011 | Dukesherer et al. |
| 8,034,071 B2 | 10/2011 | Scribner et al. |
| 8,080,000 B2 | 12/2011 | Makower et al. |
| 8,088,101 B2 | 1/2012 | Chang et al. |
| 8,090,433 B2 | 1/2012 | Makower et al. |
| 8,100,933 B2 | 1/2012 | Becker |
| 8,123,722 B2 | 2/2012 | Chang et al. |
| 8,142,422 B2 | 3/2012 | Makower et al. |
| 8,172,828 B2 | 5/2012 | Chang et al. |
| 8,190,389 B2 | 5/2012 | Kim et al. |
| 8,233,963 B2 | 7/2012 | Hartmann et al. |
| 8,277,478 B2 | 10/2012 | Drontle et al. |
| 2004/0064150 A1 | 4/2004 | Becker |
| 2005/0143724 A1 | 6/2005 | El-Galley et al. |
| 2006/0004286 A1 | 1/2006 | Chang et al. |
| 2006/0229549 A1 | 10/2006 | Francischelli et al. |
| 2008/0125720 A1* | 5/2008 | Kim ........................ A61B 1/313 604/177 |
| 2008/0172033 A1* | 7/2008 | Keith .................. A61B 1/00154 604/506 |
| 2008/0195041 A1* | 8/2008 | Goldfarb ............... A61M 29/02 604/96.01 |
| 2008/0200927 A1 | 8/2008 | Hartmann et al. |
| 2010/0030113 A1 | 2/2010 | Morriss et al. |
| 2010/0274188 A1* | 10/2010 | Chang .................... A61B 1/227 604/96.01 |
| 2010/0280363 A1 | 11/2010 | Skarda et al. |
| 2010/0312101 A1* | 12/2010 | Drontle .................. A61B 17/24 600/424 |
| 2010/0312338 A1* | 12/2010 | Gonzales ............... A61B 17/24 623/10 |
| 2011/0021975 A1 | 1/2011 | Covello |
| 2011/0060214 A1 | 3/2011 | Makower |
| 2011/0264134 A1 | 10/2011 | Drontle et al. |
| 2011/0270081 A1 | 11/2011 | Burg et al. |
| 2012/0010646 A1 | 1/2012 | Keith et al. |
| 2012/0046542 A1 | 2/2012 | Csavoy et al. |
| 2012/0108954 A1 | 5/2012 | Schulhauser et al. |
| 2012/0172912 A1 | 7/2012 | Ressemann et al. |
| 2012/0197110 A1 | 8/2012 | Hartmann et al. |
| 2012/0259217 A1 | 10/2012 | Gerrans et al. |

FOREIGN PATENT DOCUMENTS

| | | |
|---|---|---|
| WO | 9420166 | 9/1994 |
| WO | 2012039905 | 3/2012 |
| WO | 2012133115 | 10/2012 |
| WO | 2013116050 | 8/2013 |
| WO | 2013155409 | 10/2013 |

* cited by examiner

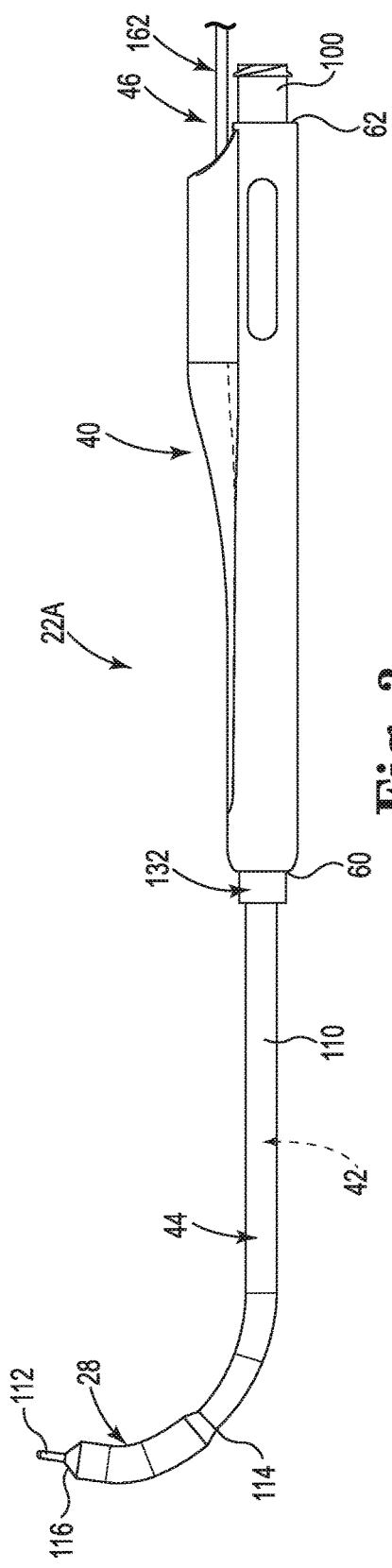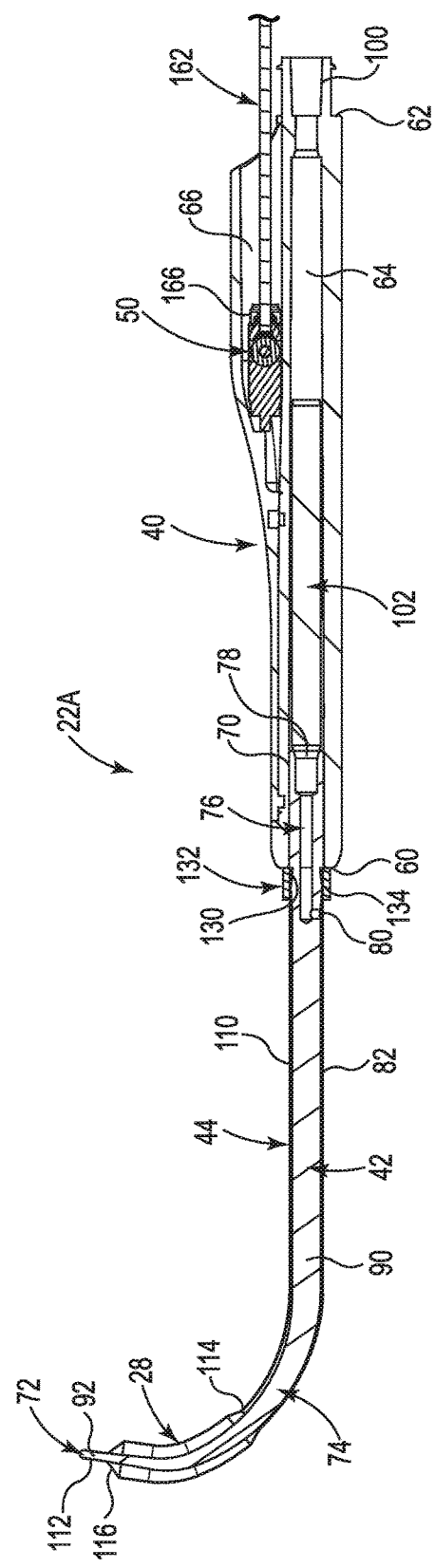

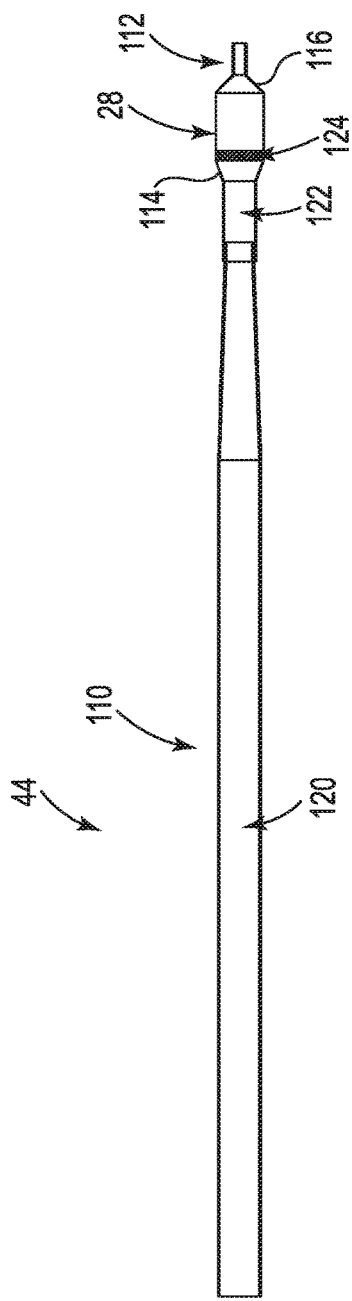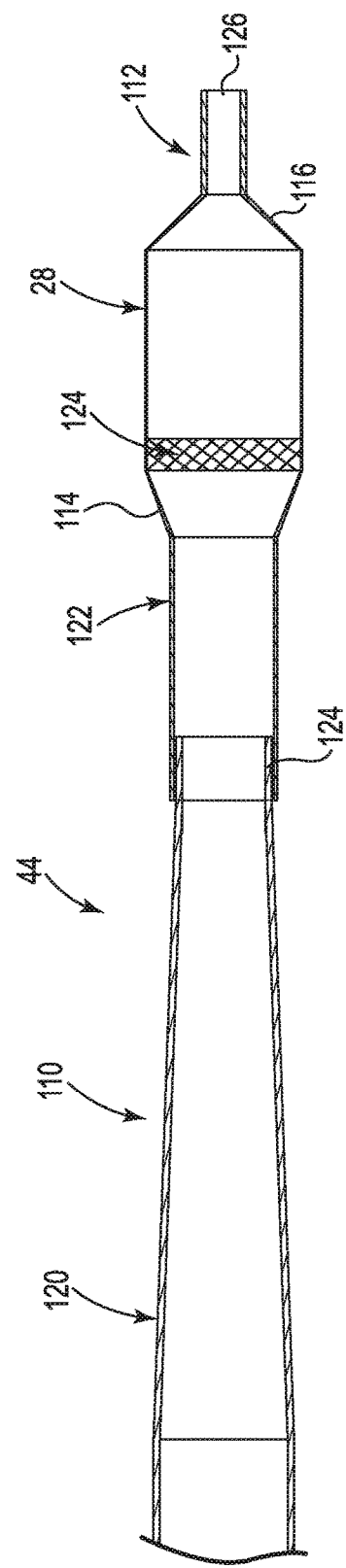
Fig. 5A
Fig. 5B

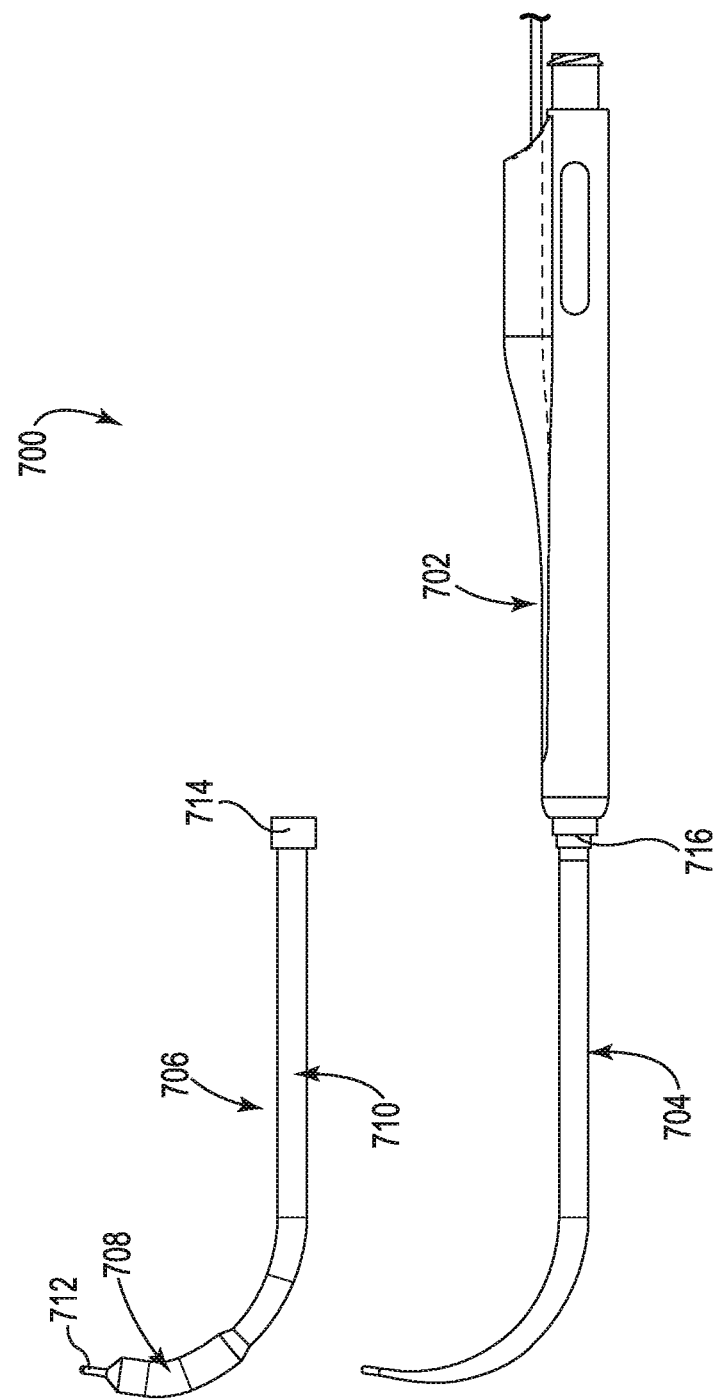

SINUS DILATION SYSTEM AND METHOD

CROSS-REFERENCE TO RELATED APPLICATIONS

This application is a continuation of U.S. application Ser. No. 13/725,716, filed Dec. 21, 2012, which is now U.S. Pat. No. 9,463,307 entitled "Sinus Dilation System and Method"; the entire teachings of which are incorporated herein by reference.

BACKGROUND

The present disclosure relates to sinus dilation systems and methods. More particularly, it relates to minimally invasive, balloon-based systems and methods for dilating a portion of a patient's paranasal sinuses in the treatment of sinusitis and other disorders.

The paranasal sinus system is a grouping of four pairs of air-filled cavities that are named for the facial bones in which they are located. The maxillary sinuses surround the nasal cavity, the frontal sinuses are above the eyes, the ethmoid sinuses are between the eyes, and the sphenoid sinuses are within the sphenoid bone at the center of the skull base under the pituitary gland. The paranasal sinuses are lined with respiratory epithelium, are joined to the nasal cavity via small orifices called ostia, and contain secretory tissue that produces a large volume of mucus. This mucus is normally relieved from the sinuses in a specific pattern through the corresponding ostia.

The mucus membrane that lines the paranasal sinuses can become inflamed. This inflammation is known as sinusitis (or rhinosinusitis), and can be caused by various factors such as bacteria, viruses, allergies, anatomical abnormalities, etc. If the mucosa of one of the paranasal sinus passageways becomes inflamed, the passageway can become blocked, trapping mucus. Patients suffering from sinusitis can experience a number of symptoms or complications, such as headache, facial pain, toothache, inner ear problems, etc.

Sinusitis is typically classified as acute (infection lasting 4 or less weeks) or chronic. Many instances of acute sinusitis can be effectively treated with medication (e.g., antibiotics, antihistamines, etc.). Chronic sinusitis may implicate a more invasive treatment option in which the paranasal passageways or affected sinuses are surgically accessed. Conventional sinus surgery entails an incision formed along the side of the nose or through the gums of the upper teeth to provide access to the targeted sinus anatomy. Once accessed, the paranasal sinus passageway in question is surgically enlarged or otherwise altered to facilitate resumption of mucus clearance.

More recently, corrective sinus surgery has been performed endoscopically, minimizing external trauma to the patient. With functional endoscopic sinus surgery (FESS) an endoscope is inserted into the nose. Using visualization through the endoscope, the anatomical and pathological obstructions associated with the sinusitis are removed in order to restore normal mucus clearance. The benefit of FESS (and other intranasal procedures) is the ability to allow for a more targeted approach to the affected sinuses, reducing tissue disruption and minimizing post-operative complications.

An even more recent minimally invasive, intranasal sinus surgery is known as balloon sinus dilation or balloon sinuplasty. Balloon sinus dilation (or simply "sinus dilation") was initially developed to address the post-operative pain and bleeding associated with FESS. In general terms, conventional sinus dilation is an endoscopic, catheter-based procedure for treating sinusitis using a small, flexible balloon catheter to enlarge the affected sinus passageway(s). When the balloon is correctly located and inflated, it widens the walls of the sinus passageway, with the goal of restoring normal drainage without damaging the sinus lining.

When performing sinus dilation, the surgeon inserts a sinus guide catheter or cannula through the nostril (or naris) to gain access to the affected sinus ostia (opening) under endoscopic visualization. A guide wire and/or illumination system are then introduced into the targeted sinus via the sinus guide catheter. Once access to the intended targeted location is confirmed by light or fluoroscopy, a flexible catheter, carrying a balloon, is introduced into the sinus cavity over the sinus guide wire, locating the balloon in the blocked ostium. In this regard, the illumination system provides transcutaneous (through the skin) light transmission that the surgeon relies upon when estimating desired balloon placement. Once the desired balloon position has been visually confirmed, the balloon is gradually inflated to dilate the narrowed or blocked ostium. The balloon is then deflated and removed. Next, an irrigation catheter may be advanced over the guide wire to flush out mucus. Finally, the sinus irrigation catheter is removed from the sinus to allow the sinus cavity to drain any mucus.

While highly promising, existing sinus dilation systems and methods have several drawbacks. As highlighted by the above, available sinus dilation systems require multiple steps and multiple instruments. For example, some available sinus dilation systems require eighteen steps to complete a sinus dilation procedure. While the guide wire can facilitate accessing the targeted sinus site and use of a flexible balloon catheter, surgeons must be trained in the correct use of the guide wire, and the guide wire represents an added cost. Further, the required illumination source and use thereof is time-consuming and relatively expensive. Moreover, a surgeon is required to estimate a location of the targeted ostium only by illumination through the patient's skin. In some instances, the guide wire and/or illumination source may inadvertently be located in a "blind hole". As a point of reference, regions of the sinus system are pneumatized by various cells in most patients. These cells can build over time, collectively creating an anatomic variation. In some instances, for example, Type II cells can occur at the frontal sinus and can progress to a level that is grossly akin to the frontal sinus ostium. It is estimated that as many as 25% of patients suffering from sinusitis of the frontal sinus have Type II cells. When internally illuminated (and viewed externally), a region of the Type II cell cluster may appear (or "feel") quite similar to the natural frontal sinus ostium opening, leading the surgeon to incorrectly assume that the desired ostium has been accessed. When the balloon is subsequently inflated, it may actually occlude the ostium rather than open the ostium.

In light of the above, the need exists for improved sinus dilation systems and methods.

SUMMARY

Some aspects in accordance with principles of the present disclosure relate to a surgical system for dilating a region of a patient's nasal sinus system. The system includes a surgical sinus dilation instrument having a handle, a rigid probe, and a balloon. The rigid probe is attached to the handle and extends distally therefrom. The probe defines a proximal end, a distal tip opposite the proximal end, and a curved segment between the proximal end and the distal tip.

The balloon is secured to the probe adjacent the distal end, with an interior of the balloon being fluidly connected to an inflation path. A curvature and longitudinal location of the curved segment is configured to locate the balloon within one of a frontal, maxillary, or sphenoid sinus when inserted through a naris or other conventional sinus approach (e.g., canine fossa or open approach) of a patient. A connector is associated with the handle and is configured to be electronically coupled to a navigation or image guidance system (IGS). The terms "navigation system", "information guidance system" and "IGS" are used interchangeably throughout this disclosure. Finally, an electronic identifier device is electronically coupled to the connector and is programmed to generate a signal indicative of an instrument identification assigned to the sinus dilation instrument. The instrument identification corresponds with the region of the patient's nasal sinus system the instrument is configured (e.g., specifically configured) to access and treat with the balloon. In this regard, the assigned instrument identification is one of a frontal sinus instrument, a maxillary sinus instrument, or a sphenoid sinus instrument. With this construction, a surgeon seeking to perform a sinus dilation procedure simply connects the sinus dilation instrument to an IGS via the connector. The IGS automatically recognizes the particular format/instrument identification assigned to the instrument, as well as the dimensional features thereof. In other words, once coupled, the IGS directly or indirectly "knows" the spatial location of the balloon or other relevant portion/component of the instrument (e.g., the IGS can be programmed to determine a spatial location of a distal tip of the shaft, where the balloon is secured in close proximity to the distal tip, the balloon location is thus also indirectly "known"). During the subsequent sinus dilation procedure, images generated by the IGS readily inform the surgeon of the balloon location as the instrument's probe is inserted into the nasal passageways and directed toward the targeted sinus region. The balloon is inflated to dilate the ostium, then deflated and removed from the patient. Systems and methods of the present disclosure entail minimal components and are easily used.

In some embodiments, the system includes first-third sinus dilation instruments each having the curved, rigid probe and electronic identifier described above. The rigid probe of a first one of the instruments is configured for a frontal sinus procedure, the second instrument's probe for a maxillary sinus procedure, and the third instrument's probe for a sphenoid sinus procedure. When presented as a set or kit to a surgeon, the surgeon need only select the instrument shaped for the particular procedure in question, and then connect the selected instrument to the IGS.

BRIEF DESCRIPTION OF THE DRAWINGS

FIG. 3 is a side view of the frontal sinus dilation instrument of FIG. 2;

FIG. 4 is a cross-sectional view of the frontal sinus dilation instrument of FIG. 2;

FIG. 5A is a side view of a sheath useful with the instrument of FIG. 2;

FIG. 5B is an enlarged cross-sectional view of a portion of the sheath of FIG. 5A;

FIG. 13 is a simplified side view of another sinus dilation instrument in accordance with principles of the present disclosure.

DETAILED DESCRIPTION

Figure 1:
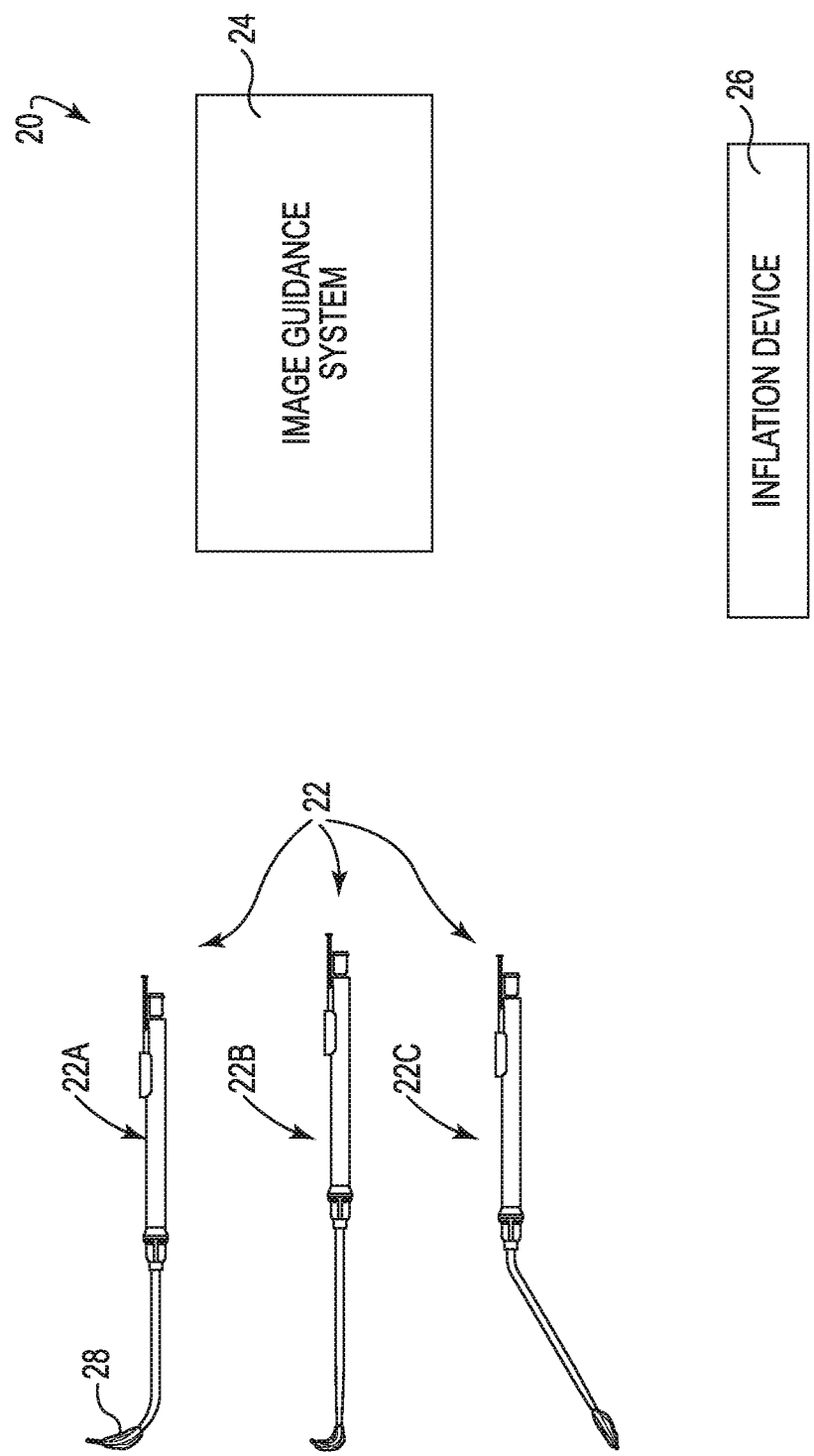
FIG. 1 is a schematic illustration of a surgical sinus dilation system in accordance with principles of the present disclosure and with portions shown in block form.

One embodiment of a surgical sinus dilation system 20 in accordance with principles of the present disclosure is shown in FIG. 1. The system 20 includes one or more sinus dilation instruments 22, an image guidance system ("IGS") 24 and an inflation device 26. The components are described in greater detail below. In general terms, however, the instrument 22 is sized and shaped for locating a balloon 28 (identified for the instrument 22A in FIG. 1) carried thereby at a particular targeted sinus region (e.g., frontal sinus, maxillary sinus, or sphenoid sinus) via a patient's naris (or alternatively sized and shaped for accessing the targeted sinus region through other conventional approaches such as canine fossa or open approach). Further, the instrument 22 is configured to electronically interface with the IGS 24, with the IGS 24 programmed to automatically recognize size and shape attributes of the instrument 22. Finally, the inflation device 26 is selectively fluidly connected to the instrument 22, and operates to effectuate inflation and deflation of the balloon 28. With this construction, use of the system 20 in treating the paranasal sinus system of a patient entails electronically coupling the instrument 22 to the IGS 24. Once connected, the IGS 24 provides the surgeon with visual representations indicative of the balloon 28 relative to the patient's anatomy (e.g., a "crosshair" icon representing the distal tip of the instrument 22 superimposed on images of the patient's anatomy) as the surgeon maneuvers the instrument 22 to bring the balloon 28 to the paranasal sinus target site. The inflation device 26 is operated to inflate the balloon 28, thereby expanding the sinus ostium (or other region of the accessed sinus) as desired. Following deflation of the balloon 28, the instrument 22 is removed from the patient and the procedure is complete. In some embodiments, the system 20 includes two or more of the sinus dilation instruments 22, each sized and shaped for accessing a different sinus region of a patient (via an intranasal approach). Once the surgeon has determined the paranasal sinus to be treated, the surgeon selects the appropriately sized and shaped sinus dilation instrument, electronically (wired or wireless) connects the selected instrument 22 with the IGS 24, and then performs the procedure as outlined above. The IGS 24 automatically "recognizes" the selected instrument 22 and generates imaging information based upon the now known spatial parameters of the instrument being used.

Figure 2:
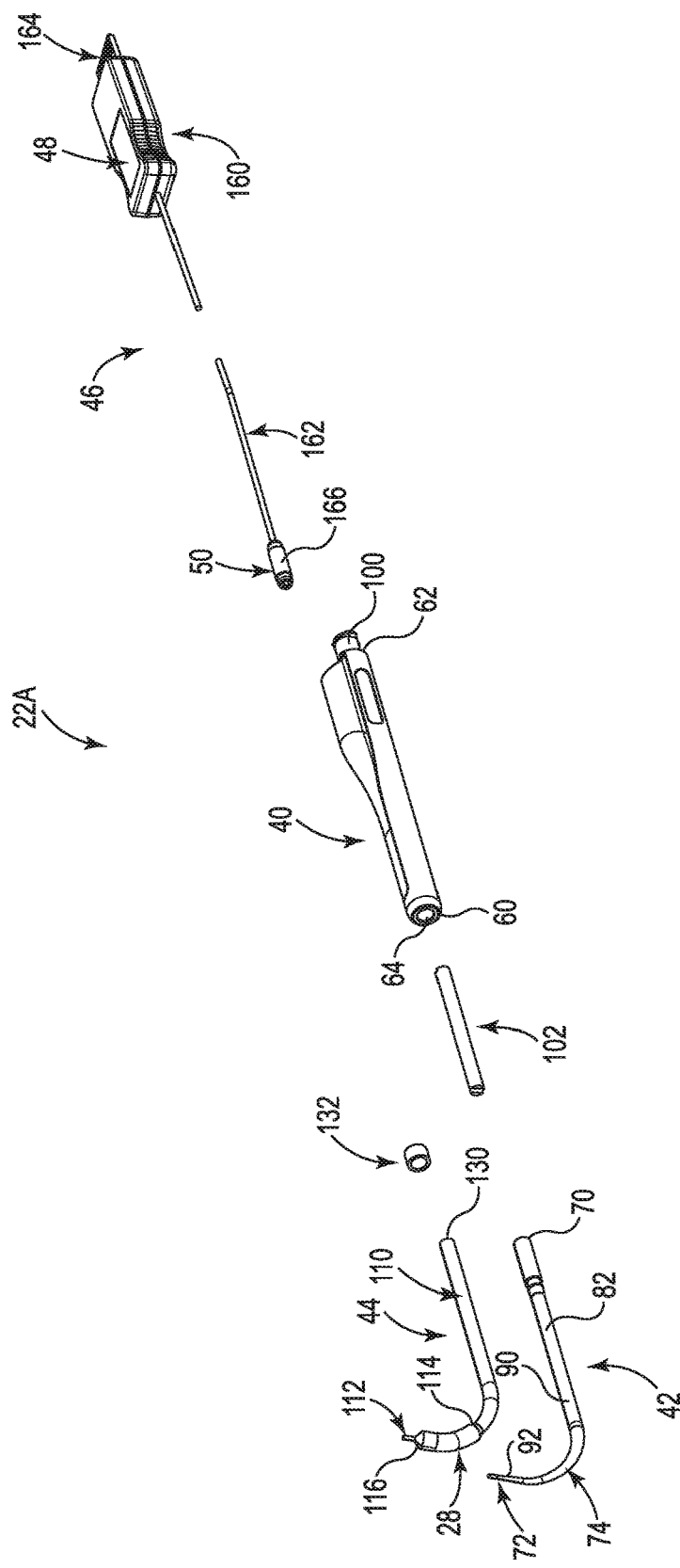
FIG. 2 is an exploded perspective view of a frontal sinus dilation instrument useful with the system of FIG. 1.

One embodiment of a sinus dilation instrument 22A useful with the system 20 is shown in FIGS. 2-4, and is configured or formatted (e.g., specifically configured or formatted) for performing a frontal sinus procedure. The instrument 22A includes a handle 40, a rigid probe or shaft 42, a sheath 44 providing the balloon 28, an IGS connector assembly 46, an identifier device 48 (referenced generally), and a tracking device 50. In general terms, the rigid probe 42 is attached to the handle 40 and carries the balloon 28. The IGS connector assembly 46 extends from the handle 40 and is adapted for electronic coupling with the IGS 24 (FIG. 1). The identifier device 48 is configured to electronically store instrument identification information indicative of a particular sinus location or sinus procedure assigned to the instrument 22A (i.e., frontal sinus). Further, the identifier device 48 is electronically connected to, or provided as part of, the IGS connector assembly 46 such that when the IGS connector assembly 46 is coupled to the IGS 24, the instrument identification information generated by the identifier device 48 is communicated to the IGS 24. The IGS 24, in turn, is programmed to recognize the instrument identification information provided by the identifier device 48 and reference known geometries of the instrument 22A. The IGS 24 can further facilitate use of the instrument 22A in performing a sinus dilation procedure by referencing information provided to or from the tracking device 50.

The handle 40 can assume a variety of forms and in some embodiments is formed of a hardened, surgically safe material such as plastic or metal. While the handle 40 can have the generally cylindrical, streamlined shape shown, any other shape conducive to grasping and manipulating by a user's hand is equally acceptable.

As described in greater detail below, the handle 40 can incorporate various features configured to interface with or retain other components of the instrument 22A. In more general terms, the handle 40 forms or defines a leading end 60, a trailing end 62, a passageway 64, and a cavity 66 (FIG. 4).

The rigid probe 42 is mounted to the handle 40, and is formed of a rigid, surgically safe material such as stainless steel (e.g., hard tempered stainless steel). While the handle 40 and the rigid probe 42 have been illustrated and described as being separately formed and subsequently assembled to one another, in other embodiments the handle 40 and the rigid probe 42 are integrally formed as a single, homogenous body. As best shown in FIGS. 2 and 4, the rigid probe 42 is an elongated body defining a proximal end 70, a distal tip 72, and an intermediate, curved segment 74. In some embodiments and as identified in FIG. 4, the rigid probe 42 further forms an inflation lumen 76 extending from a proximal end opening 78 to a side port 80 that is otherwise fluidly open to an exterior surface 82 of the probe 42.

The curved segment 74, as well as a longitudinal length of the rigid probe 42, is configured for accessing the frontal sinus via the naris (such that the instrument 22A can also be referred to as a "frontal sinus dilation instrument"). In this regard, the rigid probe 42 can be mounted to the handle 40 in a variety of manners (insert molded, adhesive, welded, press fit, etc.), with the rigid probe 42 extending distally from the leading end 60 of the handle 40. For example, as shown in FIG. 4, the handle 40 is press fit over the rigid probe 42 such that the proximal end 70 is encompassed within the handle 40 (e.g., the proximal end 70 is lodged within the passageway 64). With this construction, a spatial location of the curved segment 74 and the distal tip 72 relative to the leading end 60 is designed to be appropriate for accessing (via the naris or other conventional approach) the frontal sinus and locating the curved segment 74 at the ostium or narrow drainage path of the frontal sinus.

The rigid probe 42 defines a proximal section 90 and a distal section 92 at opposite sides of the curved segment 74, and in some embodiments the proximal section 90 extends in a linear fashion from the leading end 60 to the curved segment 74. Alternatively, one or more bends can be formed along the proximal section 90. The distal section 92 can have a linear shape in extension from the curved segment 74 to the distal tip 72. As a point of reference, the rigid probe 42 can include features between the proximal section 90 and the proximal end 70 that facilitate assembly to the handle 40. For example, a region 94 can have an enlarged diameter (as compared to a diameter of a remainder of the rigid probe 42) sized for press fit engagement with the handle 40.

A shape of the curved segment 74 can be defined in terms of an angular relationship the curved segment 74 establishes between the proximal section 90 and the distal section 92. For example, the distal section 92 is orientated 70°-120° to the proximal section 90, alternatively 85°-105°. In related embodiments, the distal tip 72 is off-set from a centerline of the proximal section 90 by a distance in the range of 22-42 mm. Regardless, the curved segment 74 has a radius of curvature and bend angle appropriate for locating the distal tip 72 at or adjacent a frontal sinus ostium (it being understood that the frontal sinus typically does not have a distinct ostium as otherwise found with the maxillary and sphenoid sinuses; instead, the frontal sinus "ostium" is akin to a narrow drainage path) of a typical adult patient when the distal tip 72 is inserted through the naris and manipulated through the corresponding paranasal sinus passageways. For example, the curved segment 74 may have two or more distinct bends, with the predominant bend having a continuous radius of curvature in the range of 14-34 mm, and a bend angle in the range of 78°-118°. In related embodiments, it has surprisingly been found that providing the curved segment 74 with two distinct bends (as shown best in FIG. 6A), with the distal-most bend locating the distal tip 72 at a bend angle of less than 90°, a "reverse bend" is effectuated by the curved segment 74 and serves as a safety feature in that as the rigid probe 42 is directed toward the frontal sinus ostium, the distal tip 72 is directed away from the patient's brain.

In some embodiments, an outer diameter of the rigid probe 42 tapers along at least a portion of the curved segment 74 to the distal tip 72. With these constructions, the outer diameter at the proximal section 90 is greater than the outer diameter at the distal tip 72. In other embodiments, the rigid probe 42 can have a more uniform outer diameter. Regardless, a rigidity of the rigid probe 42 (e.g., as dictated by a material, construction and/or outer diameter of the rigid probe 42) robustly maintains a spatial position of the distal tip 72 relative to the handle 40, and in particular relative to the leading end 60. For example, where the handle 40 is held stationary and a force of 1 lb is applied to the distal tip 72 in a direction opposite a curvature of the curved segment 74, the curved segment 74 will deflect no more than 1 mm. Alternatively, the rigid probe 42 can exhibit an enhanced stiffness, or may be slightly less rigid, along the curved segment 74. As used throughout the specification, however, the term "rigid probe" specifically excludes a conventional, flexible catheter.

To maintain the above-described rigidity or stiffness, the rigid probe 42 is a solid structure along at least the curved segment 74. For example, the inflation lumen 76 has a relatively short length, and terminates in close proximity to the leading end 60 of the handle 40 such that a majority (e.g., at least 75%) of the proximal section 90, as well as an entirety of the curved segment 74 and the distal section 92, are solid in cross-section. This solid configuration provides the desired rigidity while allowing the distal tip 72 and the curved segment 74 to have a relatively small outer diameter (and thus highly conducive to intranasal insertion). Because the inflation lumen 76 terminates at a location well-spaced from the curved segment 74 and the balloon 28 is located along the curved segment 74, an inflation path to the balloon 28 is established, at least in part, at an exterior of the rigid probe 42 as described below. In other embodiments, however, the rigid probe 42 can be more akin to a tube, with the inflation lumen 76 extending to the curved segment 74 (and the rigid probe 42 incorporating other design features that provide the stiffness or rigidity characteristics described above).

In some embodiments, the handle 40 is constructed to provide access to the inflation lumen 76. For example, the handle 40 can form or include a connector port 100 (e.g., a luer connector) at the trailing end 62 that is fluidly connected to the inflation lumen 76 via the passageway 64. With these and other constructions, the proximal end 70 (and thus the proximal end opening 78) is within the handle 40. Alternatively, the rigid probe 42 can be mounted to the handle 40 such that the proximal end 70 is external the handle 40 and can directly receive auxiliary tubing (not shown) from the inflation device 26 (FIG. 1) directly at the proximal end opening 78. A variety of other port configurations are equally acceptable that facilitate fluid coupling of the inflation lumen 76 to auxiliary tubing from the inflation device 26. In some embodiments, the sinus dilation instrument 22A includes a volume element 102 disposed within the passageway 64. The volume element 102 is a generally cylindrical body having an outer diameter slightly less than a diameter of the passageway 64. Thus, inflation medium introduced at the port 100 will flow within the passageway 64, about the volume element 102, to the inflation lumen proximal end opening 78. An overall size or volume of the volume element 102 is a function of a volume of the passageway 64 and a volume of the balloon 28. More particularly, the volume element 102 compliments the size of the balloon 28 so that the apparent volume of any of the sinus dilation instruments disclosed herein will be the same. For example, an instrument with a larger balloon volume will utilize a larger volume element 102 as compared to an instrument (with the same sized passageway 64) with a smaller balloon volume. As a result, each of the instruments will have the same total volume (i.e., available internal volume within the passageway 64 (as reduced by the volume element 102) plus the volume of the balloon 28). In other embodiments, the volume element 102 can be omitted or replaced by a fluid connector.

The balloon 28 is secured over the rigid probe 42, and is comprised of a semi-compliant material (e.g., nylon, nylon derivatives, Pebax, polyurethane, PET, etc.). In some embodiments, and as best shown in FIG. 2, the balloon 28 is provided or formed as part of the sheath 44. The sheath 44 can be a homogeneous, extruded tubular body that defines the balloon 28, a base 110 and a tail 112. The base 110 extends proximally from a proximal end 114 of the balloon 28, and is generally sized and shaped in accordance with a size and shape of the rigid probe 42 (and in particular the proximal section 90) for reasons made clear below. Similarly, the tail 112 extends distally from a distal end 116 of the balloon 28, and is sized and shaped to receive the distal tip 72 of the rigid probe 42.

The balloon 28 can be defined along a length of the sheath 44 in various manners, and is generally characterized as being more readily expandable than the base 110 and the tail 112. One construction of the sheath 44 is shown in greater detail in FIGS. 5A and 5B. As a point of reference, the sheath 44 is shown in the exploded view of FIG. 2 as exhibiting a self-maintained curvature; as reflected in FIGS. 5A and 5B, however, the sheath 44 as a standalone component need not have a definitive curvature but instead is sufficiently flexible to generally follow or conform to a shape or curvature of the rigid probe 42 (FIG. 2) upon final assembly. The sheath 44 can be formed by first and second sections 120, 122. The sections 120, 122 are tubular, and can be separately formed and subsequently assembled in completing the sheath 44. The first section 120 defines a majority of the base 110, and can taper in diameter at a leading end 124. The second section 122 forms the balloon 28, the tail 112, and a small portion of the base 110. The sections 120, 122 can be bonded to one another as shown. As best reflected in FIG. 5B, a wall thickness of the sheath 44 along the balloon 28 is less than the wall thickness along the base 110 and the tail 112. With this configuration, the proximal and distal ends 114, 116 of the balloon 28 are effectively defined by a transition in wall thickness of the sheath 44 from the thinner balloon 28 to the thicker base 110 and tail 112. Due to the increased wall thickness, the base 110 and the tail 112 experience minimal, if any, expansion when the sheath 44 is subjected to expected operational inflation pressures (e.g., 12 ATM or less). Further, the balloon 28 expands to, but not beyond, a preformed size and shape reflected in FIG. 5B at the expected operational inflation pressures. In some embodiments, the balloon 28 is configured to have a maximum outer diameter upon inflation of about 7 mm, alternatively about 6 mm, alternatively about 5 mm, and to maintain this pre-determined maximum outer diameter upon inflation at inflation pressures up to at least 10 ATM.

The balloon 28 optionally includes a marker 124 at or adjacent the proximal end 114 (e.g., the marker 124 is a band etched into a material of the balloon 28 on a full diameter of the balloon 28 at or adjacent the proximal end 114). The marker 124 thus serves as a visual identifier as to a location of the balloon 28 relative to a length of the rigid probe 42 (FIG. 2) upon final assembly. For example, where the marker 124 is located at the proximal end 114 of the balloon 28, when the surgeon sees the marker 124 almost entering the targeted ostium (e.g., via endoscopic visualization), s/he has confirmation that the balloon 28 is in the ostium.

Figure 6A:
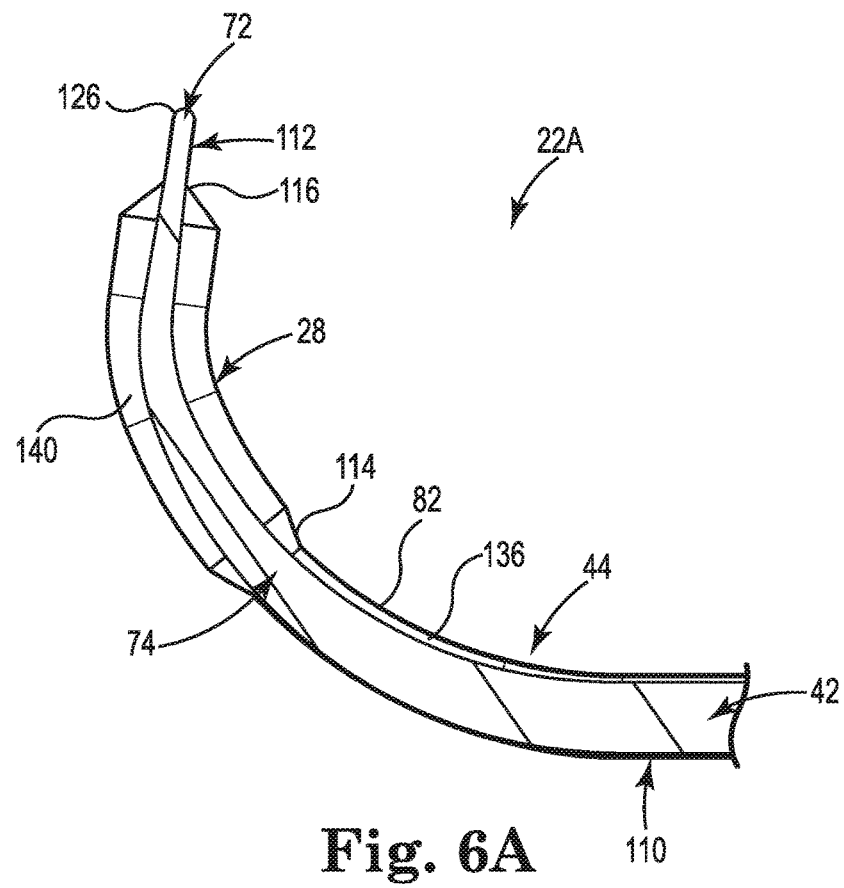
FIG. 6A is an enlarged view of a portion of the instrument of FIG. 4.

The tail 112 can assume various forms conducive to mounting with the rigid probe distal tip 72 (FIG. 2). For example, and as best shown in FIG. 5B, the tail 112 can be a tube terminating at an open end 126. An inner diameter of the tail 112 approximates an outer diameter of the rigid probe distal tip 72 such that the tail 112 can nest over the distal tip 72. Other constructions are also acceptable and the tail 112 can alternatively be closed at the end 126. With reference between FIGS. 2 and 4, the sheath 44 is sized and shaped in accordance with the rigid probe 42 such that sheath 44 can be fully assembled over the rigid probe 42. More particularly, the rigid probe 42 is loaded into the sheath 44 until the distal tip 72 is nested within the tail 112, and the base 110 surrounds the proximal section 90. As shown in FIG. 6A for example, the tail 112 is received over the distal tip 72, with the open end 126 located along a length of the distal tip 72. The tail 112 is attached to an exterior of the distal tip 72 in a sealed manner, for example by bonding the tail 112 to the distal tip 72. Alternatively or in addition, a sealing body (e.g., a domed cover) can be inserted over the tail 112 to effectuate a more secure affixment of the tail 112 to the distal tip 72. In other embodiments, a bond body can be molded over the distal tip 72 and provides a material surface approximate for bonding with the tail 112. Various other techniques and corresponding mounting assemblies capable of securing the tail 112 with the distal tip 72 in a sealed manner are also envisioned.

FIG. 6A further reflects that upon final assembly, the sheath 44 generally conforms to a shape of the rigid probe 42, following a curvature of the curved segment 74 as well as the tapering outer diameter of the distal tip 72. As a point of reference, FIG. 6A illustrates the balloon 28 in the inflated or expanded state. Due to the curvature of the curved segment 74, the sheath base 110 may be slightly displaced from an interior side of the curvature of curved segment 74 and/or portions of the inflated balloon 28 may not be centered relative to the rigid probe 42. However, a concentric relationship of the balloon 28 relative to the rigid probe 42 does not affect use of the balloon 28 in performing a sinus dilation procedure as described below. Further, the balloon 28 consistently expands or inflates to the predetermined shape regardless of whether the balloon 28 remains centered about the rigid probe 42.

Figure 6B:
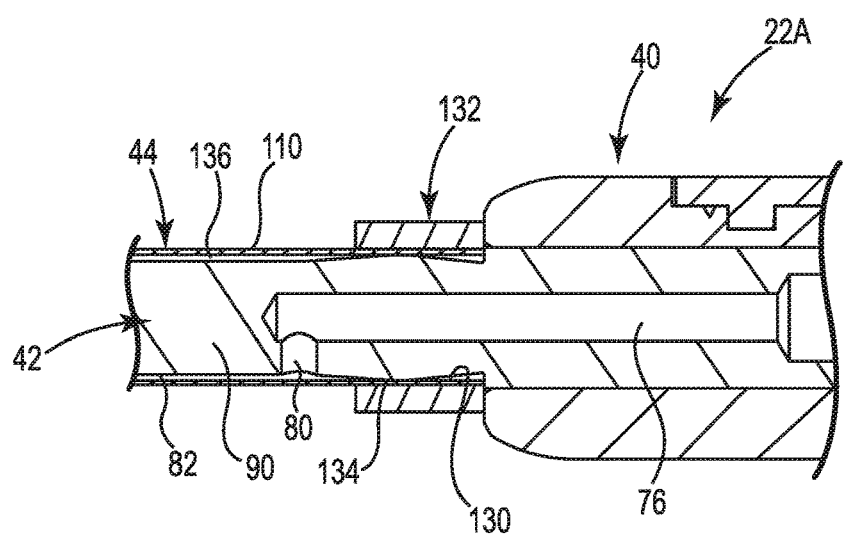
FIG. 6B is an enlarged view of another portion of the instrument of FIG. 4.

Returning to FIGS. 2 and 4, a proximal side 130 of the sheath 44 is secured to the exterior surface 82 of the rigid probe 42 in a fluid tight manner by a ring 132 or other device (e.g., adhesive). Regardless, a seal 134 is defined between the sheath 44 and the exterior surface 82, with the seal 134 being located proximal the side port 80 as shown in FIG. 6B. With this arrangement, an inflation path 136 is defined between the exterior surface 82 and the sheath 44, extending along the base 110 to the balloon 28 (FIG. 6A). Further, the inflation path 136 continues to the balloon 28 as identified in FIG. 6A. As a point of reference, an inner diameter of the sheath base 110 is, in some embodiments, only slightly greater than the outer diameter of the rigid tube proximal section 90 as reflected in FIGS. 2 and 6B.

Figure 7:
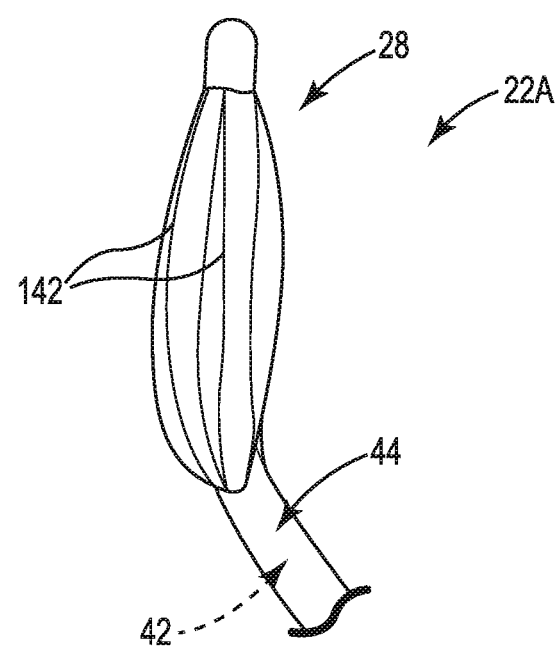
FIG. 7 is an enlarged view of a portion of the instrument of FIG. 2, illustrating a balloon in a deflated state.

With the above constructions, the balloon proximal and distal ends 114, 116 are not directly bonded to the exterior surface 82 of the rigid probe 42. Thus, an inflation region 140 is defined for the balloon 28 that is fluidly open to the inflation path 136 (e.g., because the proximal end 114 of the balloon 28 is not bonded to the rigid probe exterior surface 82, fluid flow through the inflation path 136 can enter the inflation region 140). Other constructions that fluidly connect the balloon inflation region 140 with an inflation path are also acceptable. For example, the rigid probe 42 can form a lumen extending to the inflation region 140. Alternatively, a lumen running parallel to the rigid probe 42 (e.g., a lumen formed or carried entirely by the sheath 44) can be provided. Regardless, in some constructions, the balloon 28 forms one or more pleats 142 in the deflated (or contracted) state shown in FIG. 7. The pleats 142 promote folding of the balloon 28 onto the rigid probe 42 as the balloon 28 is deflated, thereby minimizing an outer profile of the instrument 22A along the balloon 28. Alternatively, other assembly techniques can be employed that may or may not include folds or pleats being formed in the balloon 28. Regardless, in some constructions, assembly of the balloon 28 to the rigid probe 42 provides an outer diameter on the order of 2-3 mm in the deflated or contracted state.

The IGS connector assembly 46 is configured to interface with the IGS 24 (FIG. 1) as described below, and thus can have a format selected in accordance with the particular IGS 24. In some embodiments, the IGS connector assembly 46 includes a connector 160 and a cable 162. The connector 160 carries appropriate circuitry 164 for wired coupling to the IGS 24. In other embodiments, the connector 160 can be configured for wireless interface with the IGS 24. The cable 162 forms a terminal 166 opposite the connector 160 that is assembled to the handle 40. For example, the terminal 166 can be potted within the cavity 66.

In some embodiments, the identifier device 48 is associated with the connector 160 and is electronically connected to the connector circuitry 164. For example, the identifier device 48 can be a memory chip or similar circuitry component housed within the connector 160. Alternatively, the identifier device 48 can be assembled within the handle 40. Regardless, the identifier device 48 is programmed or formatted to store or generate instrument identification information unique to the instrument 22A, and in particular identifying the instrument 22A as being a "frontal sinus dilation instrument" or specifically configured for a frontal sinus procedure. That is to say, the instrument identification assigned to the instrument 22A correlates to the region of a patient's nasal sinus system for which the instrument is configured to access and treat (i.e., the frontal sinus) with the balloon 28 via an intranasal approach (or other commonly used approach). The instrument identification information is electronically stored by the identifier device 48 in a format compatible with the IGS 24 (FIG. 1). As described below, the IGS 24 is programmed with reference data from which specific dimensional features of the so-identified instrument 22A are obtained. This information, in turn, can be utilized by the IGS 24 in various operations, such as "tracking" the instrument 22A via the tracking device 50.

In some embodiments, the tracking device 50 is an electromagnetically detectable receiver wire coil or plurality of wire coils that can either transmit an electromagnetic field or sense an electromagnetic field and generate a corresponding tracking signal utilized by the IGS 24 (FIG. 1). For example, the electromagnetic coil(s) of the tracking device 50 can be potted in the handle cavity 66, or otherwise formed as a wire wrapped around a core (e.g., formed of a solid material or air) or other axis and that can sense a magnetic field by generating a current within the wire, or transmit an electromagnetic field that can be sensed by a separate sensing or localizer coil provided with the IGS 24. Other electromagnetic sensors can be employed in addition to or as an alternative to the wire coil(s), such as magnetic resistive sensors, Hall-effect sensors, etc. The tracking device 50 can alternatively assume other formats in accordance with the navigation technology employed by the IGS 24 (e.g., an infrared tracking device, an optical tracking device, an acoustic tracking device, a radiation tracking device, a radar tracking device, etc.). With these and other constructions, a location of the tracking device 50 within the handle 40 is fixed. Because a spatial location of the distal tip 72 relative to the handle 40 is also fixed (due to the rigid construction of the rigid probe 42 as described above), a spatial location of the distal tip 72, and thus of the balloon 28 secured thereto, relative to the tracking device 50 is also fixed. As a result, tracking information provided by the tracking device 50 effectively tracks movement and positioning of the distal tip 72 (and thus the balloon 28). The tracking device 50 functions, alone or in combination with at least one additional electromagnetic coil (or other tracking-related component), to provide the position of at least a portion of the instrument 22A in three-dimensional space and in real-time during a sinus dilation or other paranasal sinus system procedure being performed on a patient. In some embodiments, the identifier device 48 is an electronic information storage device (e.g., a read only memory chip) provided apart from the tracking device 50. In other embodiments, the tracking device 50 is formatted to serve as both the identifier device and the tracking device. Additional navigation-related circuitry components can optionally be provided in alternative configurations, such as an accelerometer or other inertial sensor, such as a gyroscopic sensor.

The tracking device 50 is electronically coupled to the cable terminal 166, with the cable 162 carrying signaled information from the tracking device 50 to the connector 160. The connector 160, in turn, is thus compatible with one or more I/O receptacles included with the particular IGS 24, and can facilitate other operational interfaces between the instrument 22A and the IGS 24 (e.g., where necessary, power can be delivered to the instrument 22A via the IGS connector assembly 46).

Operation of the frontal sinus dilation instrument 22A is described in greater detail below. It will be understood, however, that the frontal sinus dilation instrument 22A is uniquely configured for frontal sinus dilation procedures. Principles of the present disclosure are similarly provided in sinus dilation instruments uniquely configured to access sinuses other than the frontal sinus, several examples of which are provided below.

Figure 8:
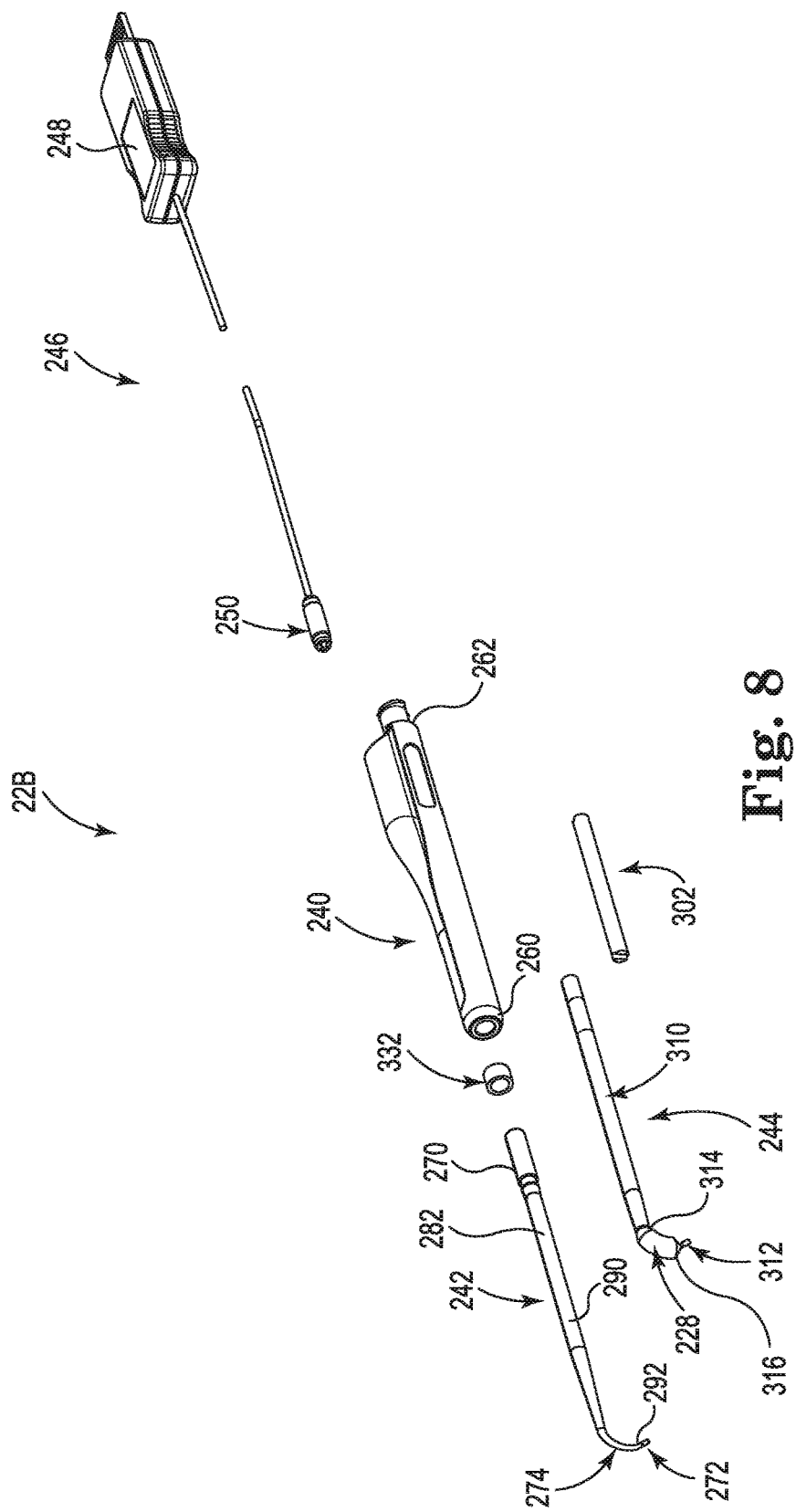
FIG. 8 is an exploded, perspective view of a maxillary sinus dilation instrument useful with the system of FIG. 1.
Figure 9:
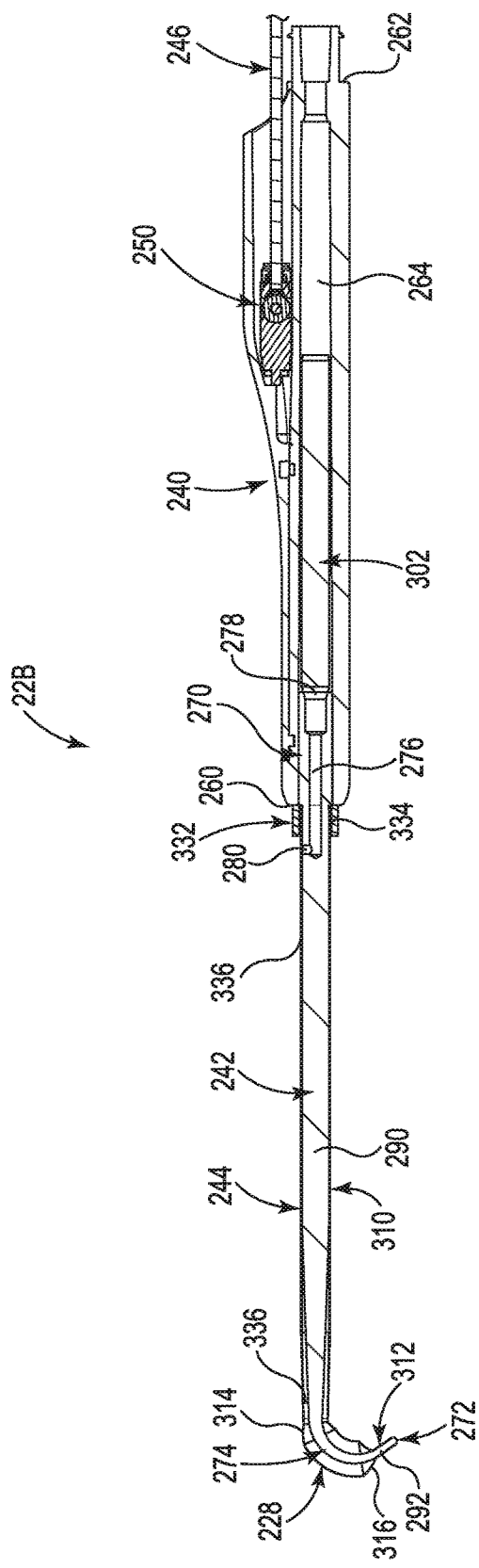
FIG. 9 is a cross-sectional view of the maxillary sinus dilation instrument of FIG. 8.

For example, another embodiment of a sinus dilation instrument 22B in accordance with principles of the present disclosure and useful with the system 20 (FIG. 1) is shown in FIGS. 8 and 9. In certain respects, the instrument 22B is highly similar to the frontal sinus dilation instrument 22A (FIGS. 2-4) described above, but is configured for a maxillary sinus procedure. With this in mind, the instrument (or "maxillary sinus dilation instrument") 22B includes a handle 240, a rigid probe or shaft 242, a sheath 244 providing a balloon 228, an IGS connector assembly 246, an identifier device 248 (referenced generally), and a tracking device 250. The rigid probe 242 projects from a leading end 260 of the handle 240, whereas the connector assembly 246 extends from a trailing end 262. The identifier device 248 is carried by the IGS connector assembly 246, and is adapted to electronically store instrument identification information indicative of the maxillary sinus designation assigned to or embodied by the instrument 22B. As a point of reference, the handle 240 and the IGS connector assembly 246 can be identical to the handle 40 and IGS connector assembly 46 (FIGS. 2-4) described above.

The rigid probe 242 is akin to the rigid probe 42 (FIGS. 2-4) described above (e.g., can be a solid metal body), and defines a proximal end 270, a distal tip 272, and an intermediate, curved segment 274. An inflation lumen 276 extends from a proximal end opening 278 to a side port 280 that is otherwise fluidly open to an exterior surface 282 of the rigid probe 242. As with previous embodiments, a portion of the rigid probe 242 can be mounted within the handle 240, with a proximal section 290 of the rigid probe 242 being defined between the leading end 260 of the handle 240 and the curved segment 274, and a distal section 292 between the curved segment 274 and the distal tip 272. In some embodiments, extension of the rigid probe 242 along the proximal section 290 and along the distal section 292 is linear. A volume element 302 can optionally be provided that effectuates a desired apparent volume in a pathway 264 to the inflation lumen 276 from an exterior of the handle 240.

The curved segment 274 has a radius of curvature and bend angle appropriate for locating the distal tip 272 at or within the maxillary sinus ostium of a typical adult patient when the distal tip 272 is inserted through the patient's naris (or other typical approach) and manipulated through the corresponding paranasal sinus passageways. For example, the curved segment 274 can have a continuous radius of curvature in the range of 1.6-9.6 mm and a bend angle in the range of 35°-75°. In other embodiments, a shape of the curved segment 274 is such that the distal section 292 is orientated 90°-140° to the proximal section 290, alternatively 110°-135°. In related embodiments, the distal tip 272 is radially off-set from a centerline of the proximal section 290 by a distance in the range of 6.4-16.4 mm. As a point of reference, the radius of curvature and bend angle of the maxillary sinus instrument's curved segment 274 is less than the radius of curvature and bend angle associated with the frontal sinus instrument's curved segment 74 (FIG. 4). As with previous embodiments, the rigid tube 242 exhibits sufficient stiffness or rigidity to resist overt deflection of the distal tip 272 in the presence of expected forces of a sinus dilation procedure.

The sheath 244 can be highly akin to the sheath 44 (FIGS. 5A and 5B) described above in terms of structure, material, and performance. The sheath 244 is formed, in some embodiments, to homogeneously generate the balloon 228 between a base 310 and a tail 312, with the sheath 244 having a reduced wall thickness along the balloon 228. The sheath 244 increases in wall thickness at proximal and distal ends 314, 316 of the balloon 228. The base 310 is sized and shaped to closely nest (e.g., fits over the rigid probe 242 with a small clearance) over the proximal section 290 of the rigid probe 242, and the tail 312 is configured to receive (and be sealed to) the distal tip 272. Upon final assembly, a ring 332 or other body (or adhesives) establishes a proximal seal 334 between the sheath 244 and the exterior surface 282 of the rigid probe 242. The proximal seal 334 is proximal the side port 280 to establish an inflation path 336 (referenced generally in FIG. 9) between the exterior surface 280 and the sheath 244 that fluidly connects the inflation lumen 276 with an interior of the balloon 228. As illustrated, at least a portion of the balloon 228 extends along the curved segment 274. As with previous embodiments, the balloon 228 is configured to expand to and maintain a preformed shape under expected inflation pressures.

The identifier device 248 can be substantially identical to the identifier device 48 (FIG. 2) described above, and can be a memory chip carried within a connector 360 of the IGS connector assembly 246 and electronically connected to connector circuitry 364. As with previous embodiments, the identifier device 248 is configured or programmed to store or generate instrument identification information indicative of the maxillary sinus designation assigned to the instrument 22B, with the IGS 24 (FIG. 1) in turn being programmed to "recognize" the maxillary sinus-related shape and dimensions associated with the instrument 22B upon connection (wired or wireless) to the connector 360 as described above. Where both of the instruments 22A, 22B are provided with the system 20 (FIG. 1), the instrument identification information embodied by the corresponding identifier devices 48, 248 each generate unique or distinct instrument identification information that is recognized by the IGS 24.

As best shown in FIG. 9, in some embodiments, the instrument 22B further includes the tracking device 250 (e.g., one or more electromagnetic coils) configured to generate tracking information that is acted upon by the IGS 24 (FIG. 1) during use of the instrument 22B in performing a maxillary sinus procedure. The instrument 22B can incorporate the tracking device 250 apart from the identifier device 248 (e.g., the identifier device 248 can be a memory chip, with a separate electromagnetic wire coil(s) serving as the tracking device 250 mounted within the handle 240). In other embodiments, the electromagnetic wire coil(s) (or other tracking component) is formatted to serve as both the identifier device 248 and the tracking device 250.

Figure 10:
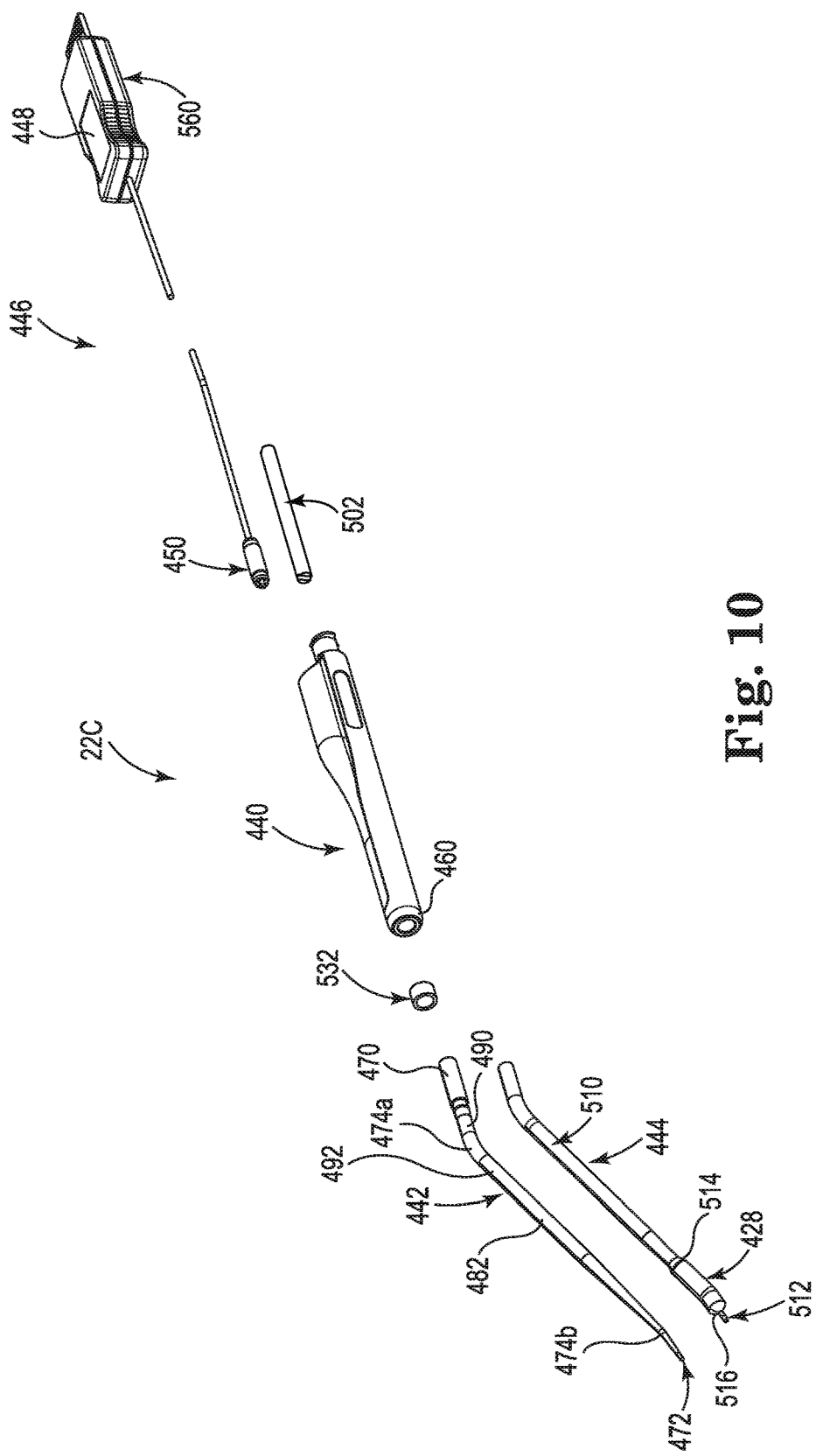
FIG. 10 is an exploded, perspective view of a sphenoid sinus dilation instrument useful with the system of FIG. 1.
Figure 11:
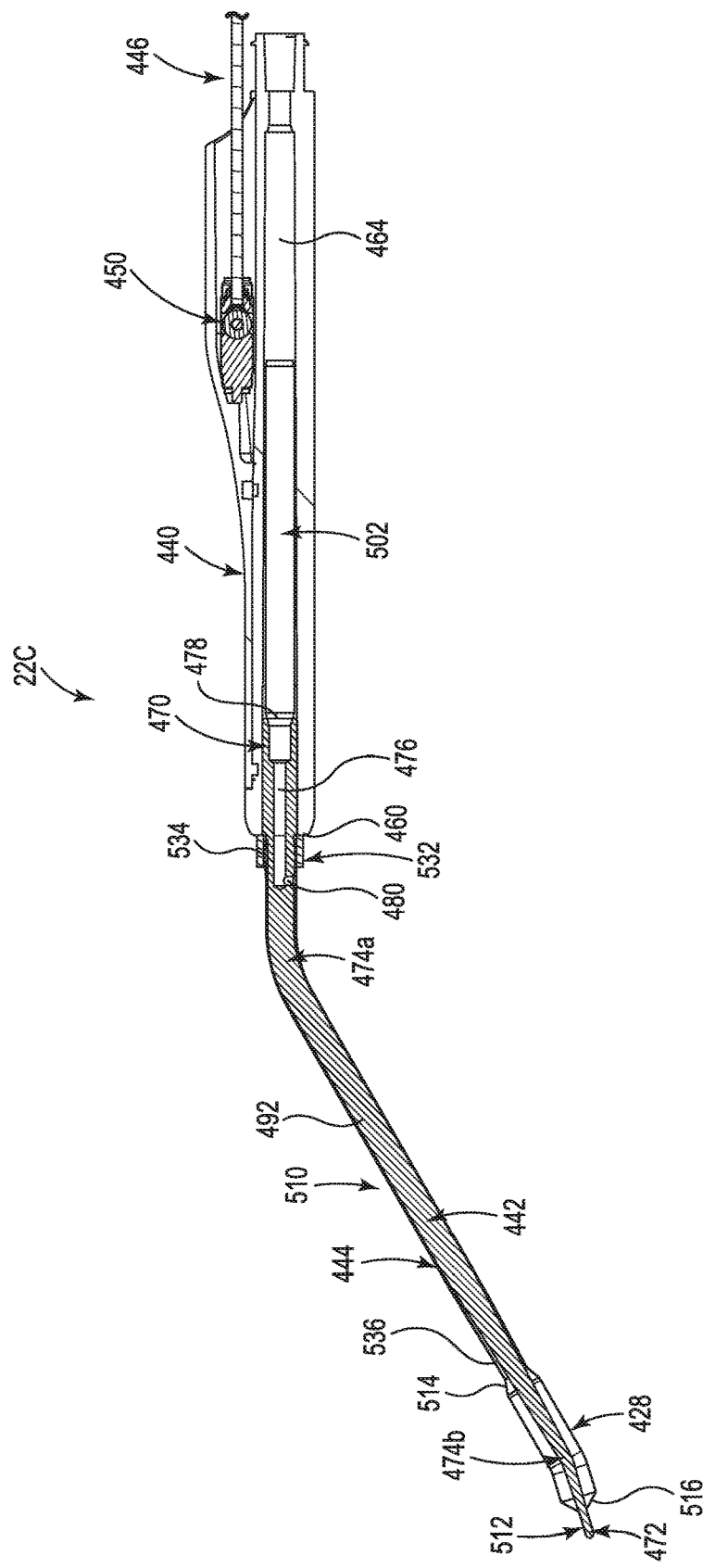
FIG. 11 is a cross-sectional view of the sphenoid sinus dilation instrument of FIG. 10.

Another embodiment sinus dilation instrument 22C in accordance with principles of the present disclosure and useful with the system 20 (FIG. 1) is shown in FIGS. 10 and 11. The instrument 22C can be, in many respects, highly similar to the instruments 22A (FIGS. 2-4) and 22B (FIGS. 8 and 9) described above, but is configured to facilitate accessing the sphenoid sinus via a patient's naris (or other conventional approach).

The instrument (or "sphenoid sinus dilation instrument") 22C includes a handle 440, a rigid probe 442, a sheath 444 providing a balloon 428, an IGS connector assembly 446, an identifier device 448 (referenced generally), and a tracking device 450. The handle 440 and the IGS connector assembly 446 can be identical to the handle 40 (FIG. 2) and the IGS connector assembly 46 (FIG. 2), respectively, described above.

The rigid probe 442 is akin to the rigid probes of previous embodiments (e.g., the rigid probe 442 can be a solid metal body), and defines a proximal end 470, a distal tip 472, a first curved segment 474a and optionally a second curved segment 474b. An inflation lumen 476 extends from a proximal end opening 478 to a side port 480 that is otherwise fluidly open to an exterior surface 482 of the rigid probe 442. The proximal end 470 can, in some embodiments, be mounted within the handle 440, with the rigid probe 442 projecting distally from a leading end 460 of the handle 440. A volume element 502 can optionally be provided that effectuates a desired apparent volume in a pathway 464 to the inflation lumen 476 from an exterior of the handle 440. The first curved segment 474a is located between a proximal section 490 and a distal section 492, and is configured to locate the distal tip 472 at or within the sphenoid sinus ostium when the distal tip 472 is inserted through an adult patient's naris (or other conventional approach) and manipulated through the corresponding paranasal sinus passageways. With the sphenoid sinus dilation instrument 22C, the first curved segment 474a is longitudinally spaced from the distal tip 472 (as compared to the frontal sinus dilation instrument 22A and the maxillary sinus dilation instrument 22B), and in some constructions the proximal and distal sections 490, 492 are linear. Where provided, the second curved segment 474b is formed adjacent the distal tip 472.

The first curved segment 474a can have a continuous radius of curvature in the range of 12.8-22.8 mm and a bend angle in the range of 10°-50°. In other embodiments, a shape of the first curved segment 474a is such that the distal section 492 is orientated 125°-175° to the proximal section 490, alternatively 140°-160°. Where provided, the second curved segment 474b can have a bend angle in the range of 8°-18°, for example 13°. Regardless, the distal tip 472 is radially off-set from a centerline of the proximal section 490 by a distance in the range of 26.6-66.6 mm.

The sheath 444 can be highly akin to the sheath 44 (FIGS. 2-4) described above in terms of structure, material, and performance. The sheath 444 homogeneously forms the balloon 428 between a base 510 and a tail 512, with the sheath 444 having a reduced wall thickness along the balloon 428. The sheath 444 increases in wall thickness at proximal and distal ends 514, 516 of the balloon 428. The base 510 is sized and shaped to closely nest (e.g., stretch) over the proximal section 490 of the rigid probe 442, and the tail 512 is configured to receive (and be sealed to) the distal tip 472. Upon final assembly, a ring 532 or other body establishes a proximal seal 534 between the sheath 444 and the exterior surface 482 of the rigid probe 442. The proximal seal 534 is proximal the side port 480 to establish an inflation path 536 (referenced generally in FIG. 12) between the exterior surface 480 and the sheath 444 that fluidly connects the inflation lumen 476 with an interior of the balloon 428. The balloon 428 can be longitudinally displaced from the first curved segment 474a and can be along the second curved segment 474b as shown.

The identifier device 448 can be highly akin to the identifier devices described above, and in some embodiments is a memory chip carried within a connector 560 of the IGS connector assembly 446. Once again, the identifier device 448 is configured or programmed to store or generate instrument identification information indicative of the sphenoid sinus designation assigned to the instrument 22C. The IGS 24 (FIG. 1) is programmed to automatically "recognize" the sphenoid instrument designation assigned to the instrument 22C upon connection (wired or wireless) with the connector 560, and distinguishes the sphenoid sinus dilation instrument 22C from the frontal sinus dilation instrument 22A (FIG. 2) and the maxillary sinus dilation instrument 22B (FIG. 9) with embodiments in which the system 20 (FIG. 1) includes each of the instruments 22A-22C.

In some embodiments, the instrument 22C further includes the tracking device 450 (e.g., one or more electromagnetic coils) configured to generate tracking information utilized by the IGS 24 (FIG. 1) during a paranasal sinus treatment procedure as described above. In some embodiments, the instrument 22C incorporates the tracking device 450 apart from the identifier device 448. Alternatively, the electromagnetic tracking coil(s) (or other tracking component) can be formatted to serve as both the identifier device 448 and the tracking device 450.

As mentioned above and returning to FIG. 1, some embodiments of the systems 20 of the present disclosure include a set or kit of surgical sinus dilation instruments, such as at least one frontal sinus dilation instrument 22A, at least one maxillary sinus dilation instrument 22B and at least one sphenoid sinus dilation instrument 22C. When preparing for a particular procedure, the surgeon selects the desired sinus dilation instrument from the set. Once connected, the IGS 24 is programmed to recognize the selected instrument 22A-22C and utilize tracking information generated by the selected instrument during a sinus procedure. For example, the instruments 22A-22C can be calibrated prior to delivery to the user and the corresponding spatial parameters stored in a memory of the IGS 24. The IGS 24 recognizes the selected instrument from the received instrument identification information and can, in some embodiments, be programmed to display a name of the selected instrument to the user. In related embodiments, the IGS 24 is programmed to further display a size of the balloon (e.g., predetermined maximum inflation diameter) to the user.

The IGS 24 can be of a type known in the art capable of tracking and providing anatomical imaging of the connected sinus dilation instrument 22 during a paranasal sinus treatment procedure. For example, the IGS 24 can be an electromagnetic-based navigation system such as the StealthStation® AxiEM™ surgical navigation system available from Medtronic Navigation, Inc. of Louisville, Colo.; a Fusion™ ENT Navigation System (electromagnetic image-guided surgery system) available from Medtronic-Xomed, Inc. of Jacksonville, Fla.; etc. Exemplary image guidance systems are also disclosed in U.S. Pat. Nos. 7,751,865; 5,913,820; and 5,592,939, the teachings of each of which are incorporated herein by reference. Other navigation technology is also acceptable, such as infrared, optical, acoustic, radiation, radar, etc. (with the sinus dilation surgical instrument's tracking device being formatted in accordance with the tracking system). In more general terms, the IGS 24 includes an instrument recognition module, a tracking module, and a display module. The instrument recognition module is programmed to interpret instrument identification information received from a selected sinus dilation instrument once electronically coupled to the IGS 24. The tracking module operates to track the sinus dilation instrument relative to a patient or within a navigation space. Finally, the display module can use image data from an imaging device (e.g., an O-arm® imaging device available from Medtronic Navigation, Inc. of Louisville, Colo.) to display on a display screen locations of the tracked instrument relative to the patient's anatomy. Thus, the IGS 24 serves to assist a surgeon in navigating the sinus dilation instrument 22 through the paranasal sinus passageways.

Various optional features of the IGS 24 are described in U.S. Publication No. 2012/0197110, the teachings of which are incorporated herein by reference. With electromagnetic tracking techniques, the tracking device associated with the sinus dilation instrument is one or more coils that can either transmit an electromagnetic field or sense an electromagnetic field to generate a tracking signal that in turn allows the tracking module of the IGS 24 to determine the location of the tracked instrument in the navigation space. Electromagnetic navigation in accordance with some aspects of the present disclosure utilizes a system that transmits three separate electromagnetic fields that are received or otherwise sensed by one or more electromagnetically detectable receiver coils integrated into the sinus dilation instrument to be tracked. At least one coil is used to monitor the three-dimensional location of that coil in three-dimensional space, as well as the sinus dilation instrument the coil is integrated with. Accurate registration of previously acquired anatomical images can be performed using one or more surface fiducial registration points, internal, implanted, and indwelling reference devices, for example. The form of reference points required to register the image to the true anatomy, if any, depends on the accuracy needed for the particular procedure and anatomy of interest.

The display module associated with the IGS 24 can assume a variety of forms and generally provides information regarding movement of the selected sinus dilation instrument relative to the patient. For example, any 2D, 3D or 4D imaging device, such as isocentric fluoroscopy, bi-plane fluoroscopy, ultrasound, computed tomography (CT), multi-slice computed tomography (MSCT), T1 weighted magnetic resonance imaging (MM), T2 weighted Mill, high frequency ultrasound (HIFU), positron emission tomography (PET), optical coherence tomography (OCT), may also be used to acquire 2D, 3D or 4D pre-or post-operative and/or real-time images or image data of the patient.

Because the paranasal sinus dilation instruments (e.g., the instruments 22A-22C) of the present disclosure incorporate a rigid probe carrying a balloon, the tracking device (e.g., wire coil) associated with each of the instruments can be mounted within the corresponding handle yet still provide viable tracking information relative to the instrument's distal tip (and thus the balloon carried thereby). Stated otherwise, a spatial location of the probe's distal tip (and thus the balloon) relative to the handle (and thus relative to the tracking device carried by the handle) will not change over the course of a particular paranasal sinus access procedure, unlike conventional balloon catheter-based sinus dilation techniques. As such, the tracking coil can assume a known, and thus relatively inexpensive, construction, and is easily and readily assembled to the handle. The sinus dilation instruments of the present disclosure are therefore cost effective and provide consistent, viable image navigation information.

Sinus dilation methods in accordance with some embodiments of the present disclosure can entail the surgeon receiving a set or kit of sinus dilation instruments comprising the frontal sinus dilation instrument 22A, the maxillary sinus dilation instrument 22B, and the sphenoid sinus dilation instrument 22C. The surgeon evaluates the paranasal sinus to be treated, and then selects the corresponding sinus dilation instrument from the set. For example, where the patient requires dilation of the ostium of one (or both) of the patient's maxillary sinuses, the maxillary sinus dilation instrument 22B is retrieved from the set. Alternatively, a "set" of three different instruments 22A-22C need not be provided to the surgeon as a kit. The patient is prepared and arranged relative to the IGS 24 in accordance with the protocols associated with the IGS 24 being used by the surgeon. The IGS connector associated with the selected sinus dilation instrument 22A, 22B, 22C is electronically coupled (wired or wireless) to a console of the IGS 24. Upon making this connection, the instrument recognition module of the IGS 24 automatically "recognizes" the selected instrument via the received instrument identification information and accesses stored information relating to a spatial location of the balloon carried by the sinus dilation instrument relative to the corresponding tracking device. Stated otherwise, once the selected sinus dilation instrument is electronically coupled to the IGS 24, the IGS 24 automatically "knows", and thus can track, a spatial position of the probe's distal tip, and thus of the balloon, based upon tracking information generated by the tracking device otherwise provided with the instrument. Thus, systems and methods of the present disclosure effectively entail a "plug and play" technique whereby the surgeon simply selects and connects the desired sinus dilation instrument to the IGS 24 and can then begin the procedure.

Figure 12A:
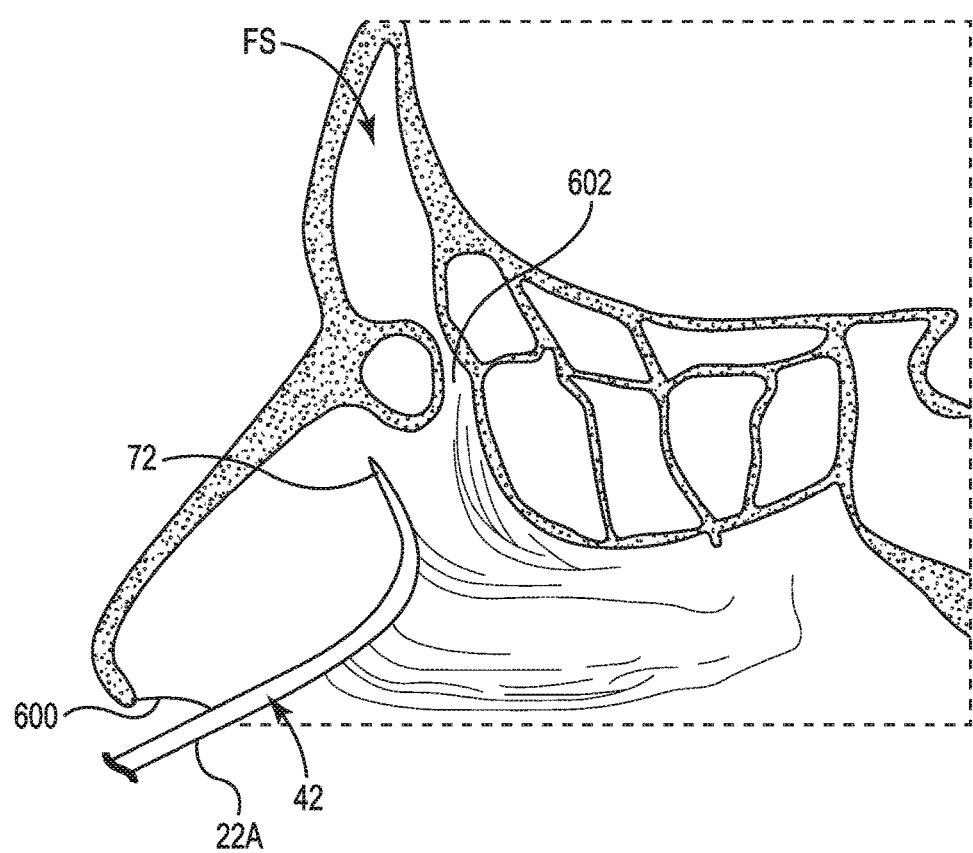
FIGS. 12A-12D illustrate use of the system of FIG. 1 in performing a sinus dilation procedure.
Figure 12B:
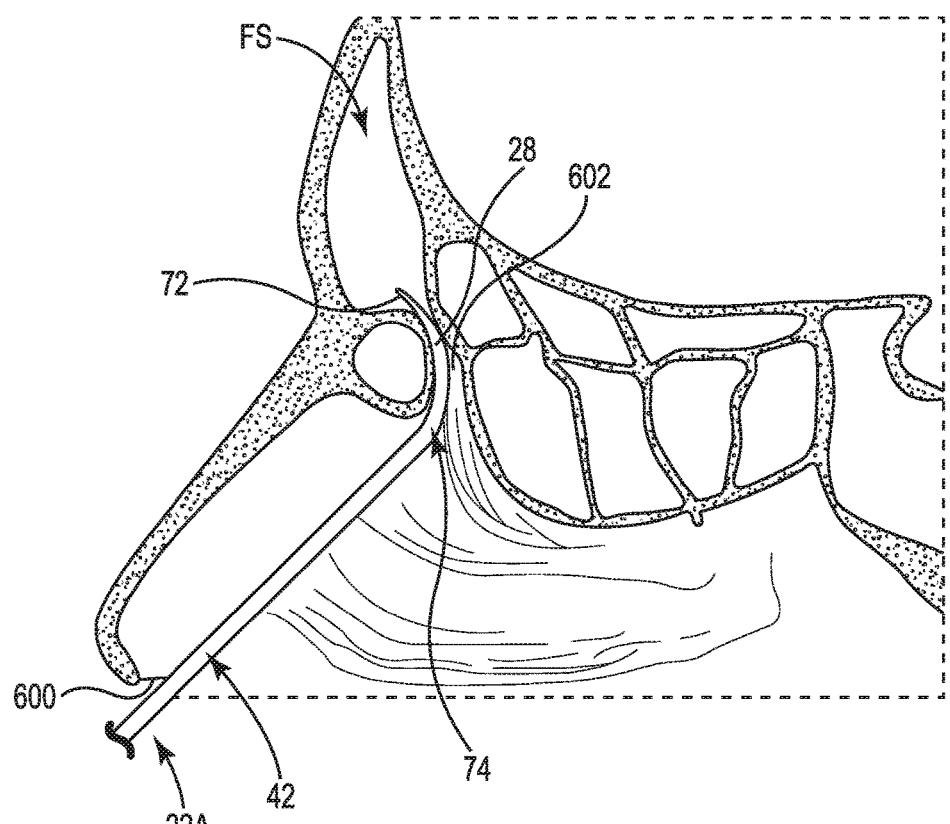

The selected sinus dilation instrument 22A, 22B, 22C is initially operated in a deflated state in which the balloon (e.g., the balloon 28 of FIGS. 2-4) is contracted about the corresponding rigid probe (e.g., the rigid probe 42 of FIGS. 2-4). The paranasal sinus to be treated is then accessed by the selected sinus dilation instrument. For example, FIGS. 12A-12D illustrate various steps of a method of accessing and dilating a frontal sinus FS using the frontal sinus dilation instrument 22A. With the surgeon grasping the instrument 22A at the handle 40 (FIG. 1), the distal tip 72 is initially introduced into the naris or nostril 600 (or other conventional approach) as shown in FIG. 12A. The rigid probe 42 is then further advanced through the patient's paranasal passageways, bringing the distal tip 72 adjacent an ostium (or narrow drainage path) 602 of the frontal sinus FS. With further advancement, and as shown in FIG. 12B, the balloon 28 is located within the ostium 602. Notably, the radius of curvature and bend angle of the curved segment 74 is configured to readily locate the balloon 28 at the frontal sinus ostium 602 via advancement through the naris 600. Throughout the transitioning of the distal tip 72 from initial insertion within the naris 600 to the final position of FIG. 12B, the IGS 24 (FIG. 1) continuously tracks movement of the frontal sinus dilation instrument 22A, and presents visual images (and/or other navigation information) indicative of the balloon 28 location relative to the patient's anatomy (e.g., a crosshair-type icon representing the distal tip 72 relative to images of the paranasal sinus passageway being traversed). Thus, with systems and methods of the present disclosure, no additional tools (e.g., guide wire) or illumination is necessary or required by the surgeon in achieving visually confirmed balloon placement at the targeted frontal sinus ostium 602. In other embodiments, an endoscope (not shown) or similar device can be employed along with the sinus dilation instrument 22A. Conventionally, the endoscope carries a camera or other visualization device that provides the surgeon with a visual display of the actual anatomy within the endoscope's field of view. With embodiments in which the balloon 28 includes the marker 124 (best shown in FIG. 5B), as the balloon 28 is being advanced into the ostium 602, once the marker 124 can no longer be seen in the endoscope's camera display, the surgeon can determine that the balloon 28 is now fully "inside" of the targeted ostium 602.

Figure 12C:
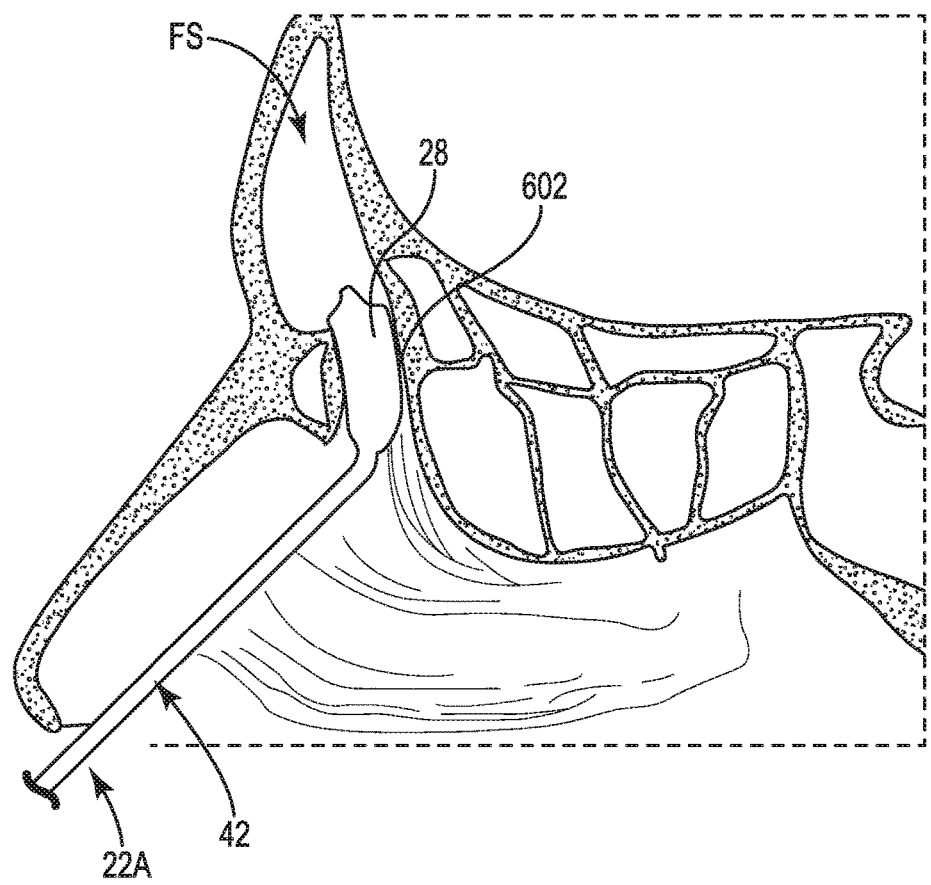
Figure 12D:
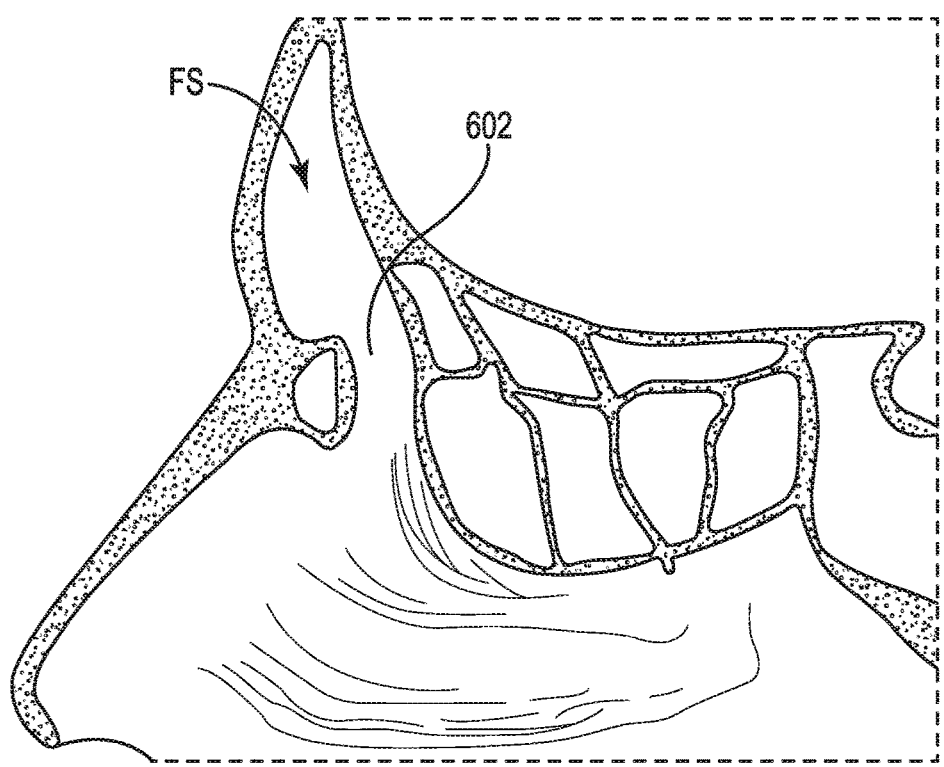

Once the balloon 28 has been desirably located relative to the ostium 602, the inflation device 26 (FIG. 1) is actuated to inflate the balloon 28 as shown in FIG. 12C. With this inflation or expansion, the ostium 602 is dilated as desired. Subsequently, the balloon 28 is deflated or otherwise contracted about the rigid probe 42, followed by withdrawal of the frontal sinus dilation instrument 22A from the patient. Upon completion of the procedure, the frontal sinus ostium 602 is dilated as shown in FIG. 12D.

Under circumstances where treatment of the patient requires dilation of other or additional sinus ostiums, the surgeon simply selects the corresponding sinus dilation instrument, connects the selected instrument to the IGS 24 (FIG. 1), and initiates accessing and dilation of the desired ostium as described above.

In some embodiments, the sinus dilation instruments 22 of the present disclosure are relatively inexpensive, disposable surgical tools (e.g., one-time use). Alternatively, in other constructions, the sinus dilation instruments can incorporate various structural features (e.g., materials, seals, etc.) that facilitate surgically-safe cleaning and sterilization (e.g., autoclave sterilization) and are re-usable. In yet other embodiments, the rigid probe 42 (FIG. 2) and the handle 40 (FIG. 2) are releasably mounted to one another. With these constructions, following a sinus dilation procedure, the rigid probe 42 (and the balloon 28 carried thereby) is removed from the handle 40, the handle 40 is sterilized, and a new rigid probe/balloon assembly mounted to the handle 40. With these alternative constructions, then, the handle 40 (and the electronic components carried by the handle 40) is re-usable. In related embodiments, the electronic components (e.g., the identifier and the tracking device) are disposable and clipped on to the handle 40 prior to use. Following completion of the procedure, the electronic components are removed, and the handle sterilized for re-use.

FIG. 13 illustrates another embodiment surgical sinus dilation instrument 700 in accordance with principles of the present disclosure and akin to the frontal sinus dilation instrument 22A (FIGS. 2-4) described above. The instrument 700 includes a handle 702, a rigid probe 704, and a sheath 706 forming a balloon 708 (shown in an expanded or inflated state). The handle 702 and the rigid probe 704 can be identical to the handle 40 (FIGS. 2-4) and the rigid probe 42 (FIGS. 2-4) described above. The sheath 706 can also be highly akin to the sheath 44 (FIGS. 5A and 5B), and forms a base 710 and a tail 712 at opposite sides of the balloon 708. With the instrument 700 of FIG. 13, however, the sheath 706 is removably attached to the handle 702/probe 704.

In particular, the base 710 terminates at a proximal collar 714. The collar 714 is sized and shaped to be sealing received within a gap 716 (referenced generally) formed between the handle 702 and the rigid probe 704. The sheath 706 is assembled over the rigid probe 704, with the collar 714 being press fit within the gap 716. The tail 712 can be formed to terminate at a closed end 716 that effectively seals against the rigid probe 704. Following use of the instrument 700, the sheath 706 can be removed, the handle 702/rigid probe 704 sterilized, and a new sheath 706 assembled over the rigid probe 704 as described above. In related embodiments, electrical components (e.g., device identifier, tracking device, and IGS connector assembly) are disposable and removably clipped to the handle 702.

Returning to FIG. 1, the inflation device 26 useful with the sinus dilation systems of the present disclosure can assume a variety of forms, and in some embodiments is a conventional syringe-type device. Saline or other surgically safe liquid can be used as the inflation medium.

Sinus dilation systems and methods of the present disclosure provide a marked improvement over previous designs. The sinus dilation instruments are specifically sized and shaped to locate the corresponding dilation balloon directly at the sinus ostium of interest without the use of additional tools or steps. Further, the sinus dilation instruments are utilized with image guidance systems not otherwise relying upon an internally deployed illumination source, and can be quickly connected to the image guidance system on a "plug and play" basis. In this regard, the image guidance system immediately "recognizes" a selected sinus dilation instrument; methods of the present disclosure effectively entail a surgeon selecting a desired sinus dilation instrument, connecting the selected instrument to the image guidance system, and then performing the procedure.

Although the present disclosure has been described with reference to preferred embodiments, workers skilled in the art will recognize that changes can be made in form and detail without departing from the spirit and scope of the present disclosure. For example, while the sinus dilation instruments have been described as including a tracking device, in other embodiments the tracking device can be omitted. Also, while the tracking device has been described as being mounted within the instrument handle, in other configurations the tracking device is mounted to or within the rigid probe.

What is claimed is:

1. A surgical system for dilating a region of a patient's nasal sinus system, the system comprising:
   a first sinus dilation instrument including:
   a handle defining a front end opposite a back end;
   a rigid probe extending distally from the front end of the handle, the rigid probe defining:
   a rigid proximal end at the front end of the handle,
   a rigid distal tip opposite the proximal end,
   a rigid curved segment between the proximal end and the distal tip;
   a balloon having a distal end, the balloon being secured over the rigid probe adjacent the distal tip, wherein a distance between the distal end of the balloon and the distal tip is invariable;
   an inflation path fluidly connected to an interior of the balloon;
   wherein a curvature and a longitudinal location of the curved segment is configured to locate the balloon within one of a frontal sinus, a maxillary sinus, and a sphenoid sinus following insertion of the distal tip through a naris of the patient;
   a connector associated with the handle and configured to be electronically coupled to an image guidance system of the type to allow for a display of a position of the first sinus dilation instrument within the patient relative to a pre-operative image of the patient's anatomy; and
an electronic identifier device electronically coupled to the connector and programmed to generate a signal indicative of an instrument identification assigned to the first sinus dilation instrument and corresponding with a region of the patient's sinus system that the first sinus dilation instrument is configured to access and treat with the balloon, the instrument identification selected from the group consisting of a frontal sinus instrument, a maxillary sinus instrument, and a spheroid sinus instrument; and
a second sinus dilation instrument including:
a handle,
a rigid probe extending from the handle and forming a curved segment,
a balloon secured over the rigid probe adjacent a distal tip thereof and fluidly connected to an inflation path,
a connector configured to be electronically coupled to the image guidance system, and
an electronic identifier device electronically coupled to the connector and programmed to generate a signal indicative of an instrument identification assigned to the second sinus dilation instrument and selected from the group consisting of a frontal sinus instrument, a maxillary sinus instrument, and a sphenoid sinus instrument;
wherein the instrument identification of the first sinus dilation instrument is different from the instrument identification of the second sinus dilation instrument;
and further wherein the electronic identifier device of the first sinus dilation instrument is separate from the electronic identifier device of the second sinus dilation instrument.

2. The system of claim 1, wherein the balloon of the first sinus dilation instrument is exteriorly exposed and is disposed over at least a portion of the curved segment of the first sinus dilation instrument.

3. The system of claim 1, wherein the first sinus dilation instrument further includes a sheath forming the balloon of the first sinus dilation instrument and a base extending from a proximal end of the balloon of the first sinus dilation instrument, and further wherein a proximal end of the base is sealed to an exterior surface of the rigid probe of the first sinus dilation instrument.

4. The system of claim 1, wherein the first sinus dilation instrument further includes a marker band formed adjacent a proximal end of the balloon of the first sinus dilation instrument, wherein the marker band is configured to visually identify a spatial location of the balloon of the first sinus dilation instrument relative to the handle of the first sinus dilation instrument.

5. The system of claim 1, wherein the first sinus dilation instrument further includes a tracking device configured to generate tracking information that tracks movement and positioning of the balloon of the first sinus dilation instrument.

6. The system of claim 5, wherein the tracking device is an electromagnetically detectable receiver coil.

7. The system of claim 6, wherein the electromagnetically detectable receiver coil is disposed within the handle of the first sinus dilation instrument.

8. The system of claim 1, further comprising:
a third sinus dilation instrument including:
a handle,
a rigid probe extending from the handle and forming a curved segment,
a balloon secured to the rigid probe adjacent a distal tip thereof and fluidly connected to an inflation path,
a connector configured to be electronically coupled to the image guidance system, and
an electronic identifier device electronically coupled to the connector and programmed to generate a signal indicative of an instrument identification assigned to the third sinus dilation instrument and selected from the group consisting of a frontal sinus instrument, a maxillary sinus instrument, and a sphenoid sinus instrument;
wherein the instrument identification of the third sinus dilation instrument is different from the instrument identification of the first sinus dilation instrument and of the second sinus dilation instrument.

9. The system of claim 8, wherein the first sinus dilation instrument is configured for a frontal sinus procedure, the second sinus dilation instrument is configured for a maxillary sinus procedure, and the third sinus dilation instrument is configured for a sphenoid sinus procedure.

10. The system of claim 9, further comprising:
an image guidance system including a module forming a port configured to receive respective ones of the connectors, wherein the image guidance system is programmed to automatically recognize the instrument identification of the first, second, and third sinus dilation instruments.

11. The system of claim 10, wherein the image guidance system is further configured to generate images of a location of the balloon of the selected one of the first-third sinus dilation instruments relative to the patient's anatomy during operation of the system in performing a desired procedure.

12. The system of claim 1, wherein a longitudinal location of the curved segment of the first sinus dilation instrument relative to the corresponding proximal end differs from a longitudinal location of the curved segment of the second sinus dilation instrument relative to the corresponding proximal end.

13. The system of claim 1, wherein a radius of curvature of the curved segment of the first sinus dilation instrument differs from a radius of curvature of the curved segment of the second sinus dilation instrument.

14. The system of claim 1, wherein the balloon is formed by a sheath disposed over the rigid probe, and further wherein the sheath terminates in a tail configured to engage the distal tip and a collar configured to be removably secured to the handle.

* * * * *